United States Patent
Rutgers

(10) Patent No.: US 10,307,043 B2
(45) Date of Patent: Jun. 4, 2019

(54) ENDOTRACHEAL INTUBATION DEVICES

(71) Applicant: Richard Rutgers, Venice, CA (US)

(72) Inventor: Richard Rutgers, Venice, CA (US)

( * ) Notice: Subject to any disclaimer, the term of this patent is extended or adjusted under 35 U.S.C. 154(b) by 0 days.

(21) Appl. No.: 14/318,058

(22) PCT Filed: Mar. 13, 2014

(86) PCT No.: PCT/US2014/025642
§ 371 (c)(1),
(2) Date: Jun. 27, 2014

(87) PCT Pub. No.: WO2014/151392
PCT Pub. Date: Sep. 25, 2014

(65) Prior Publication Data
US 2015/0366445 A1 Dec. 24, 2015

Related U.S. Application Data

(63) Continuation of application No. 14/206,784, filed on Mar. 12, 2014, now abandoned.
(Continued)

(51) Int. Cl.
*A61B 1/00* (2006.01)
*A61B 1/005* (2006.01)
(Continued)

(52) U.S. Cl.
CPC ............ *A61B 1/0052* (2013.01); *A61B 1/005* (2013.01); *A61B 1/0057* (2013.01);
(Continued)

(58) Field of Classification Search
CPC .......... A61M 25/0133; A61M 25/0136; A61M 25/0147; A61B 1/00066; A61B 1/005;
(Continued)

(56) References Cited

U.S. PATENT DOCUMENTS 3,162,214 A 12/1964 Bazinet, Jr.
4,846,153 A 7/1989 Berci
(Continued)

FOREIGN PATENT DOCUMENTS

JP 2004313462 A 11/2004

OTHER PUBLICATIONS

International Search Report for related PCT/US2014/025642 dated Jul. 18, 2014.

*Primary Examiner* — Ryan N Henderson
(74) *Attorney, Agent, or Firm* — Epstein Drangel LLP; Robert L. Epstein

(57) ABSTRACT

The endoscope herein described has a unique steering capability allowing the highly flexible distal end of the shaft of the device to be moved to a full range angular positions without rotating the device on its long axis, thus enabling the device to be steered within the cavity of interest. The relative lengths of the control cables used to move the distal end of the bendable shaft can be changed whenever the flexible or malleable shaft is to be re-shaped to a new configuration thus preventing the distal end or the steering mechanism from assuming an undesired angular position. When used as an endotracheal device, a novel tongue retractor is described which forms an internal conduit, allowing passage of the bendable shaft of the endotracheal intubation device and an endotracheal tube therethrough. Methods for performing a tracheal intubation and changing the relative lengths of the cables are disclosed.

38 Claims, 21 Drawing Sheets

Related U.S. Application Data

(60) Provisional application No. 61/791,596, filed on Mar. 15, 2013.

(51) Int. Cl.
    *A61B 1/267*       (2006.01)
    *A61B 17/00*       (2006.01)
    *A61M 16/04*       (2006.01)
    *A61M 25/01*       (2006.01)

(52) U.S. Cl.
    CPC .......... *A61B 1/00066* (2013.01); *A61B 1/267* (2013.01); *A61B 1/2676* (2013.01); *A61M 16/0418* (2014.02); *A61M 16/0488* (2013.01); *A61M 25/0133* (2013.01); *A61M 25/0136* (2013.01); *A61M 25/0147* (2013.01); *A61B 1/00052* (2013.01); *A61B 2017/00318* (2013.01); *A61B 2017/00323* (2013.01); *A61M 16/0495* (2014.02)

(58) Field of Classification Search
    CPC ... A61B 1/0051; A61B 1/0052; A61B 1/0053; A61B 1/0055; A61B 1/0056; A61B 1/0057; A61B 1/0058; A61B 1/008; A61B 1/01; A61B 1/267; A61B 1/2673; A61B 1/2676; A61B 2017/003; A61B 2017/00318; A61B 2017/00323; A61B 2017/00327
    USPC .................. 600/139–152; 604/528; 606/1
    See application file for complete search history.

(56) References Cited

U.S. PATENT DOCUMENTS

| | | | |
|---|---|---|---|
| 4,905,666 A | 3/1990 | Fukuda | |
| 5,307,803 A * | 5/1994 | Matsuura | A61B 1/0051 138/118 |
| 5,327,881 A | 7/1994 | Greene | |
| 5,431,152 A | 7/1995 | Flam et al. | |
| 6,572,538 B2 * | 6/2003 | Takase | A61B 1/005 600/139 |
| 8,042,545 B2 | 10/2011 | Schwartz et al. | |
| 8,287,449 B2 | 10/2012 | Tanaka | |
| 2002/0153008 A1 | 10/2002 | Schwartz et al. | |
| 2005/0277875 A1 * | 12/2005 | Selkee | A61M 25/0136 604/95.04 |
| 2006/0052664 A1 * | 3/2006 | Julian | A61B 1/0053 600/146 |
| 2006/0173242 A1 | 8/2006 | Navok et al. | |
| 2006/0253197 A1 | 11/2006 | NaPier | |
| 2007/0021737 A1 * | 1/2007 | Lee | A61B 17/062 606/1 |
| 2007/0282371 A1 | 12/2007 | Lee | |
| 2008/0046000 A1 * | 2/2008 | Lee | A61B 17/29 606/205 |
| 2008/0294191 A1 * | 11/2008 | Lee | A61B 17/00234 606/205 |
| 2010/0041945 A1 * | 2/2010 | Isbell, Jr. | A61B 17/29 600/104 |
| 2010/0106183 A1 | 4/2010 | Lee et al. | |
| 2010/0228235 A1 | 9/2010 | Lee | |
| 2011/0077466 A1 | 3/2011 | Rosenthal | |
| 2011/0118550 A1 * | 5/2011 | Tulley | A61B 1/0052 600/149 |
| 2011/0265789 A1 | 11/2011 | Gabriel | |
| 2012/0253326 A1 * | 10/2012 | Kleyman | A61B 34/30 606/1 |
| 2013/0012929 A1 * | 1/2013 | Malkowski | A61B 17/29 606/1 |
| 2014/0275763 A1 * | 9/2014 | King | A61B 1/00022 600/103 |

\* cited by examiner

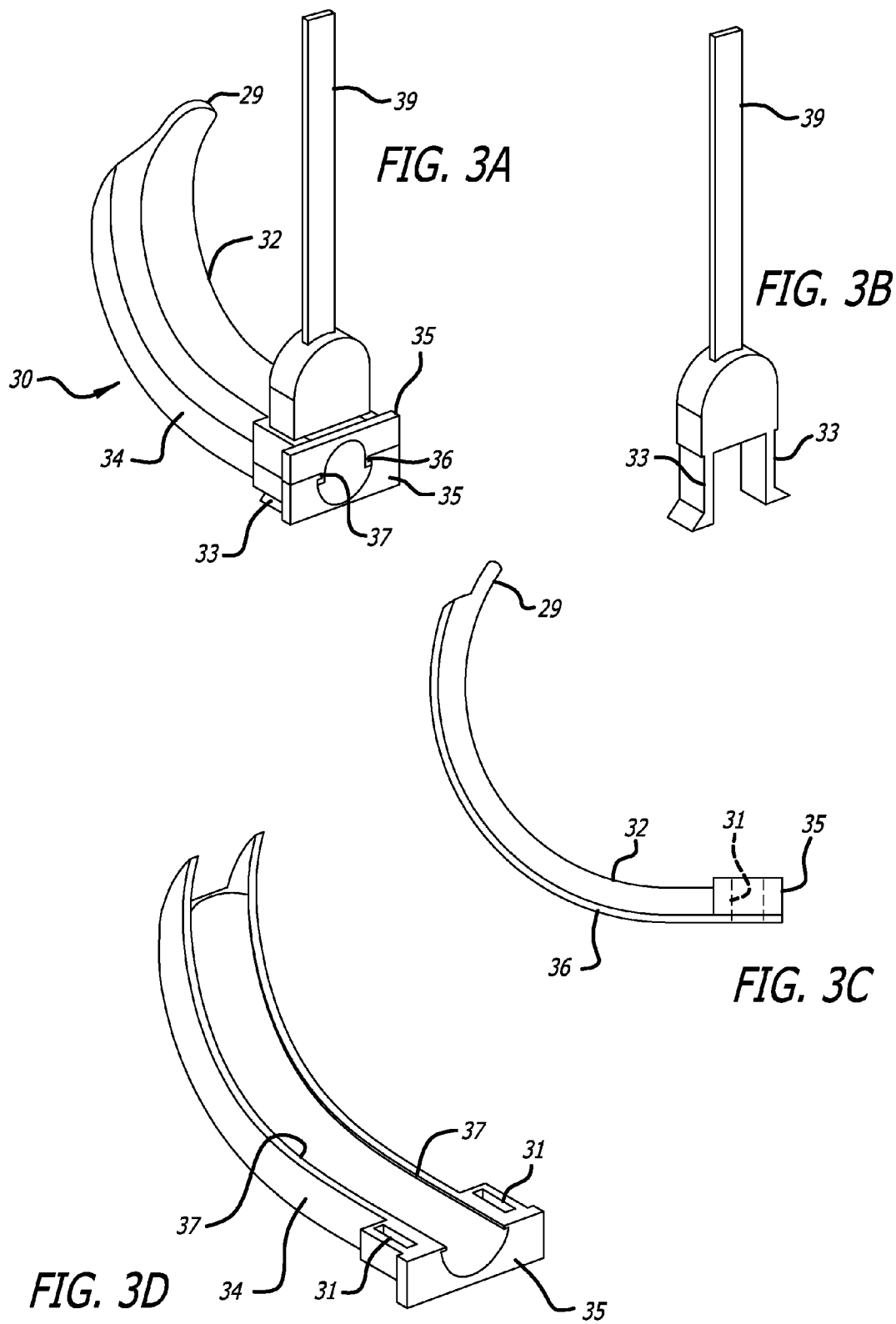

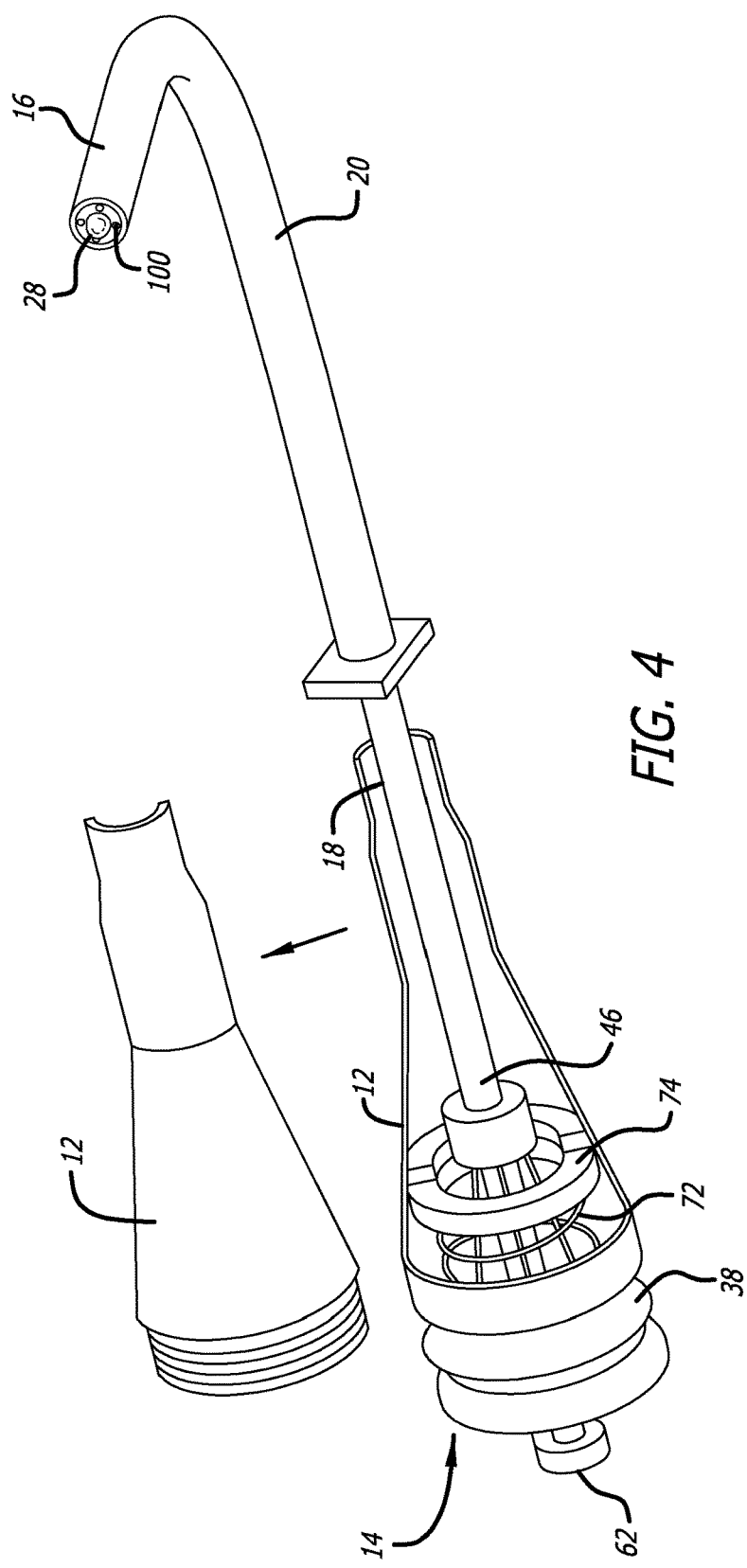

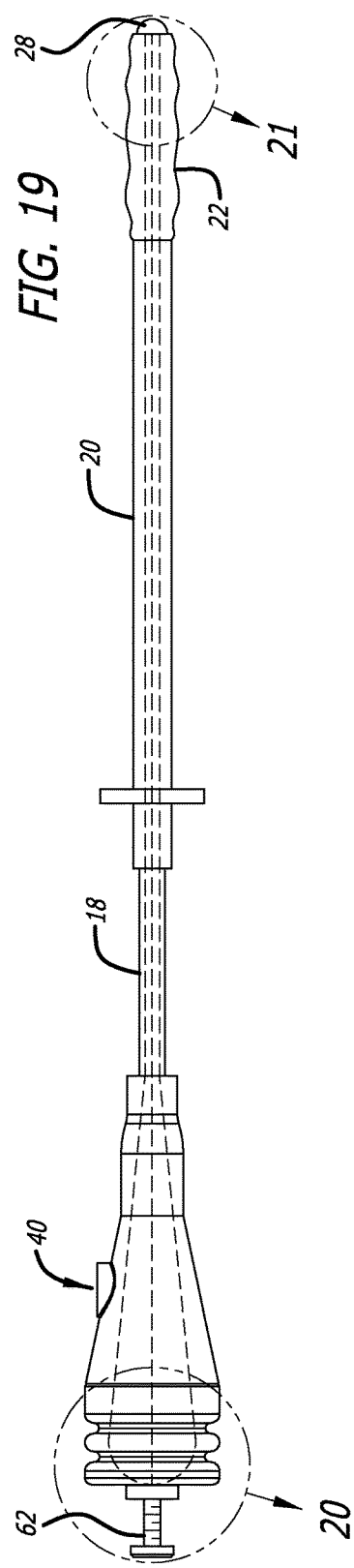
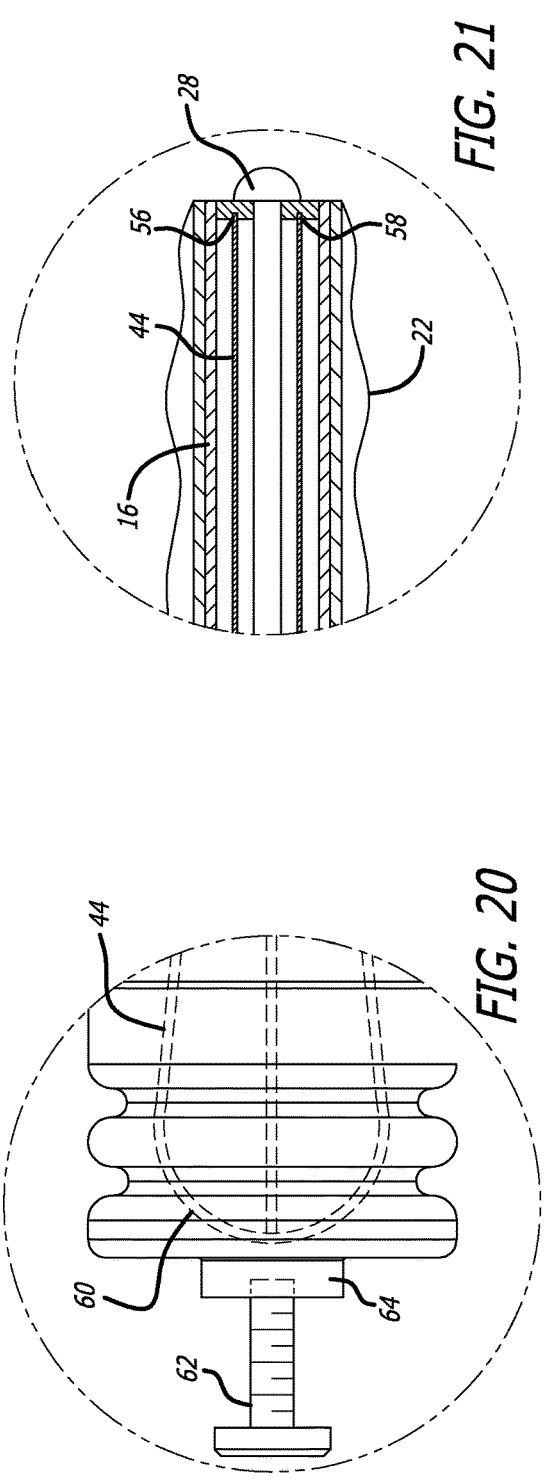
FIG. 19
FIG. 20
FIG. 21

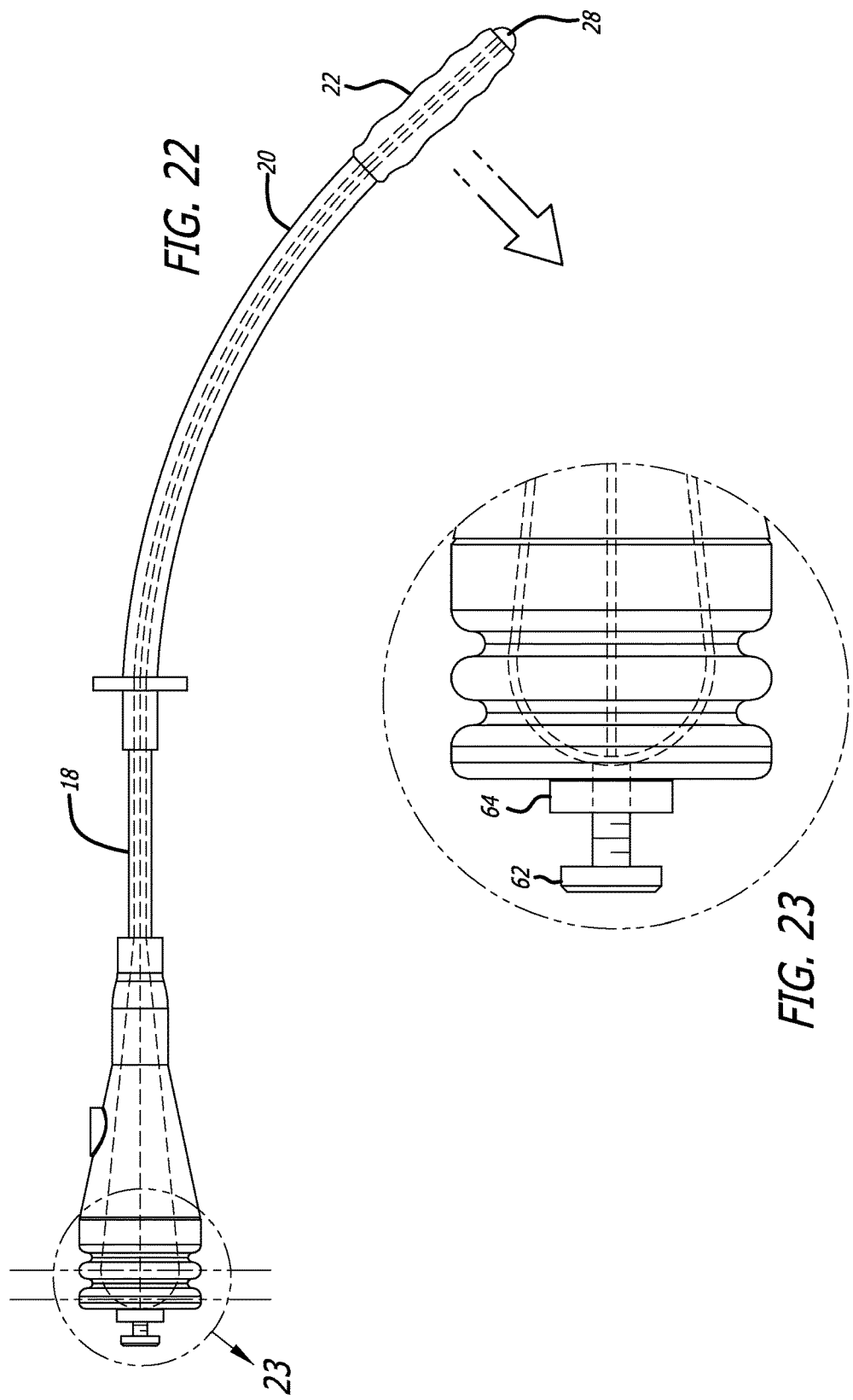

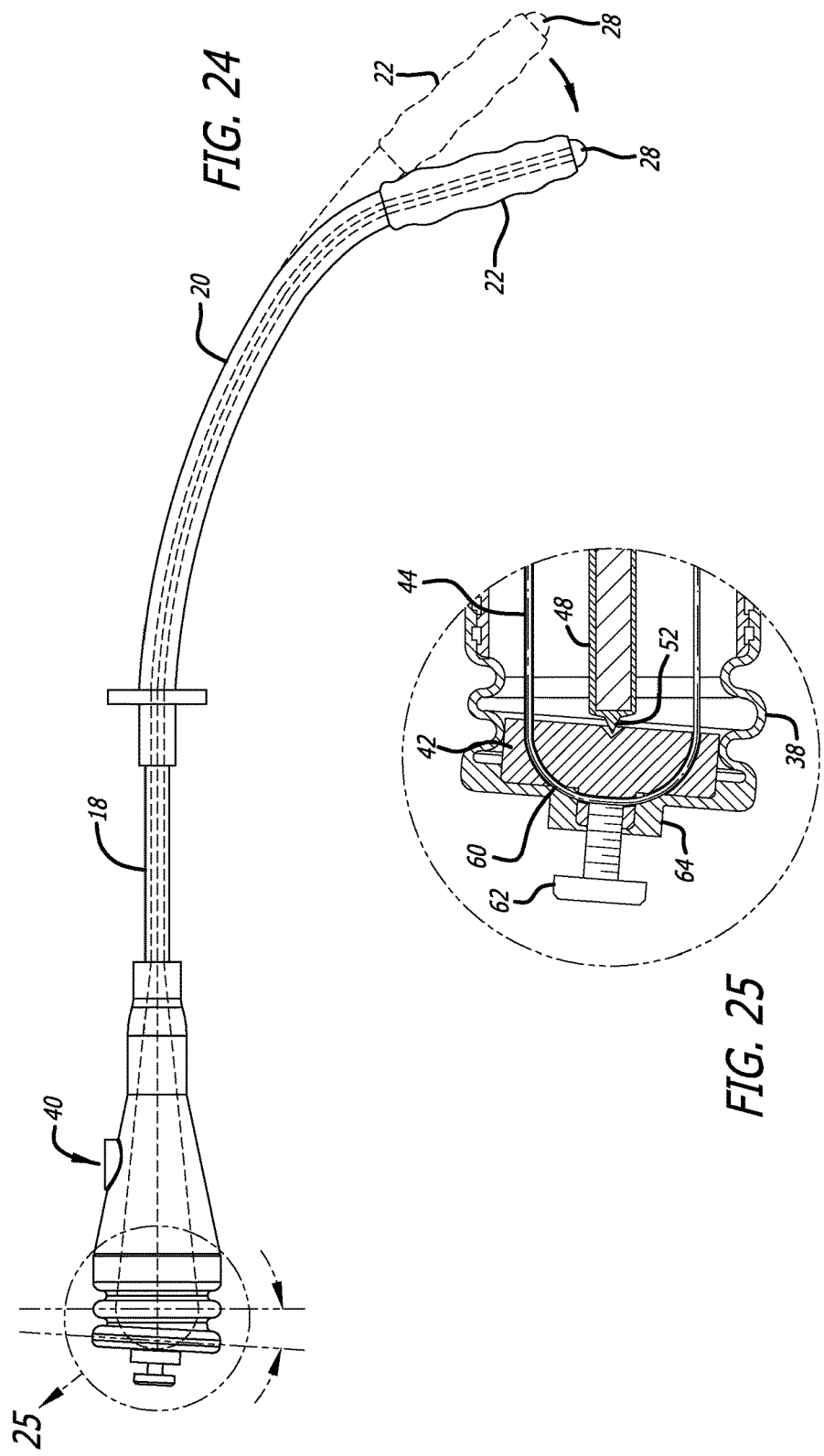

ENDOTRACHEAL INTUBATION DEVICES

CROSS-REFERENCES TO RELATED APPLICATIONS

The present application claims the benefit under 37 CFR § 119(e) of U.S. Provisional Application No. 61/791,596 filed on Mar. 15, 2013, and to PCT/US/2014025642 filed Mar. 13, 2014, the contents of which are incorporated by reference herein in their entirety.

BACKGROUND

The present invention relates generally to endoscopic devices and, more specifically, to an endotracheal intubation device having steering capability to allow the steerable distal end of the shaft of the device to be moved to a number of different angular positions to help direct the device through normal and pathologic patient anatomy. In use, an endotracheal tube is co-axially placed over the shaft of the endotracheal device so that the distal end of the endotracheal tube can be properly inserted into the trachea. The shaft of the current device may be of different rigidities, i.e., either flexible, like a conventional endoscope (colonoscope, bronchoscope, etc.) or malleable, namely, it can retain its shape once bent. Unlike other organs (colon, ureter, etc.) the oropharynx does not provide a tightly conforming conduit through which an endoscope can be passed. The flexible embodiment of the endoscope herein described can be used with a unique pre-formed conduit which allows for passage of this endoscope, with an endotracheal tube mounted on it, into the retropharyngeal space. The steerable distal end of the shaft can then be steered to position the endotracheal tube into the trachea. The present invention is also directed to methods for performing tracheal intubation.

In both medical emergencies, trauma, and as part of general anesthesia for surgery, a breathing tube is positioned in the airway of a patient. Endotracheal intubation, usually referred to as intubation, is the placement of a flexible plastic tube, an endotracheal tube or ETT into the trachea (windpipe) of the patient to maintain an open airway and to serve as a conduit through which to administer certain gases, including oxygen and anesthetic gases, directly to the lungs. It is frequently performed in critically ill, injured or anesthetized patients to facilitate ventilation of the lungs, including mechanical ventilation, and to prevent the possibility of asphyxiation or airway obstruction.

Human anatomy does not permit unaided visualization of the airway beyond the tongue. A tube passed blindly through the mouth or nose is likely to end up in the esophagus, leading to the stomach, rather than into the trachea, leading to the lungs. A variety of tools exist for performing this procedure under direct vision, which is usually performed by highly trained medical professionals in a hospital or pre-hospital setting. For the anatomical reasons stated above, namely that there is no direct line of sight from outside the mouth to the trachea, intubation involves the use of a viewing instrument of one type or another which allows the tongue to be retracted and the airway structures identified under direct vision. A modern conventional laryngoscope is most often used for intubation and consists of a handle containing batteries that power a light to visualize the target site, namely the vocal cords, which are the entry to the trachea, and a set of interchangeable blades, which are either straight or curved. With the patient on their back (supine) and the practitioner behind the patient's head, the laryngoscope is initially inserted into the patient's oral cavity. The laryngoscope blade is designed to control and move the tongue and other internal structures out of the way so that the airway can be positively identified. The vocal cords of the patient are the entry point to the windpipe (trachea) and lungs and represent the target destination through which the breathing tube (referred as an endotracheal tube) is advanced. The endotracheal tube is basically a flexible catheter that is inserted into the trachea for the primary purpose of establishing and maintaining an open and unobstructed airway. As above, endotracheal tubes are used for airway management in the settings of general anesthesia, critical care, mechanical ventilation and trauma.

Conventional intubation begins by introducing an instrument, usually a laryngoscope, into the patient's oral cavity to move the patient's tongue out of the way so that the patient's vocal cords can be identified. In practice, however, there may be anatomical anomalies and physical variations among patients which often do not permit easy direct visualization of the vocal cords. This leads to multiple attempts using different equipment. Failure to establish an airway in critically ill or anesthetized patients may lead to hypoxia (lack of oxygen), brain damage or even death in five minutes.

A conventional intubating stylet can be used in conjunction with the endotracheal tube and laryngoscope and is designed to be inserted into the internal lumen of the endotracheal tube to make the endotracheal tube, which is manufactured in a shallow "C" shape, conform better to the individual patient's anatomy and thereby facilitate steering the endotracheal tube into the trachea. This conventional stylet is in common use and can be made from a malleable metal wire, such as copper or aluminum, which allows the practitioner to impart a desired bend or shape, for example a tight "C" or a sharply angled or "hockey stick" shape, to the stylet and therefore to the overlying endotracheal tube. The stylet is typically used when the medical practitioner anticipates a difficult intubation.

During the intubation procedure, the practitioner usually holds the laryngoscope in one hand while holding the endotracheal tube and stylet, if used, with the other. The laryngoscope is used to retract the tongue and other internal structures, including the epiglottis, leading to direct visualization of the vocal cords. Once the vocal cords have been positively identified, the practitioner advances the endotracheal tube/stylet assembly so that the distal end of the endotracheal tube is inserted gently through the vocal cords and into the trachea. The stylet is then removed, leaving the endotracheal tube in the trachea and ventilation of the lungs can then be established.

While identification of the vocal cords under direct vision as described above is normally routine, there may be internal anatomical or pathological obstructions that are not apparent on visual inspection of the patient's surface anatomy. Multiple attempts at intubation may result in injury to teeth, epiglottis and vocal cords. Bleeding may result, with even less ability to visualize the airway and sometimes to obstruction of the airway, leading to hypoxia.

The endotracheal tube has a proximal fitting, or t-piece, designed to be connected to a source of pressurized gas, such as oxygen. The endotracheal tube may include an inflatable balloon (referred to as a cuff) at its distal end which is inflated once the endotracheal tube has been properly positioned within the trachea. The distal tip of the endotracheal tube should be positioned above the carina (before the trachea divides to each lung) so that both lungs can be ventilated equally. After the endotracheal tube has been inserted into the trachea, the balloon cuff is inflated to seal the airway and allow oxygen and other gases to be pumped into the lungs. This inflated balloon not only prevents retrograde leakage of respiratory gases from the lungs but also protects the tracheobronchial tree from undesirable material such as stomach acid or secretions passing antero-grade and into the lungs. The proximal end of the endotracheal tube can then be secured to the face of the patient close to the mouth and connected to the t-piece, anesthesia breathing circuit, bag valve mask device, or a mechanical ventilator. Once in place, the endotracheal tube is used to ensure the adequate exchange of oxygen and carbon dioxide, to deliver oxygen in higher concentrations than found in air, or to administer other gases such as anesthetic gases, helium, nitric oxide, or xenon.

Because it is and invasive and extremely uncomfortable procedure, intubation is most frequently performed after induction of general anesthesia. Furthermore, a neuromuscular blocking (paralyzing) drug is usually given to relax the muscles of the head and neck and facilitate intubation. However, this means that the patient has now lost his ability to breathe spontaneously and therefore ventilation must be supported by the practitioner. At this point inability to intubate or provide ventilation of the lungs can lead to grave consequences, and is the leading cause of medical malpractice claims against anesthesiologists.

As noted above, difficult tracheal intubation can be associated with complications of varying severity. There may be broken teeth or lacerations of the tissues of the upper airway. It can also be associated with potentially fatal complications such as pulmonary aspiration of stomach contents which can result in a severe and sometimes fatal chemical aspiration pneumonitis. Unrecognized intubation of the esophagus, instead of the trachea, leading to fruitless ventilation of the stomach, can lead to potentially fatal anoxia. Because of this, the potential for difficulty or complications due to the presence of unusual airway anatomy or other uncontrolled variables is carefully evaluated before undertaking tracheal intubation. However, normal surface anatomy is no guarantee of favorable internal anatomy and easy intubation, so alternative strategies for securing the airway must always be readily available.

Endotracheal intubation using a direct laryngoscope is usually a relatively easy procedure to perform by trained personnel. However, difficult cases sometimes require specially made devices to provide alternative methods for intubation. Some laryngoscopes feature specially shaped blades and the use of fiber- or video-optics for indirect visualization where direct visualization is not possible. Fiber optic laryngoscopes have become increasingly available and commonly used since the 1990's. In contrast to the conventional laryngoscope, which only afford a direct line of sight, these devices allow the medical practitioner to "see around the corner" and indirectly view the larynx. This may provide a significant advantage in those situations where the practitioner cannot obtain a direct view of the larynx and needs to see around an acute bend in the airway, caused for example by a large tongue, short lower jaw, small mouth or protruding teeth. Video laryngoscopes are specialized fiber optic laryngoscopes that use a digital video camera sensor to allow the operator to view the glottis and larynx on a video monitor.

One of the problems associated with conventional intubation devices, such as the stylet, includes the fact that once the stylet is pre-shaped by the practitioner, it cannot be additionally bent while it is placed within the patient's oral cavity. If the initial shape imparted to the stylet does not allow the endotracheal tube to be properly maneuvered into the trachea, the practitioner must remove the stylet (and mounted endotracheal tube) from the patient's pharynx, re-bend the stylet/endotracheal tube assembly to a more favorable shape, and then reintroduce the assembly back into the patient's pharynx. These steps may have to be repeated again if the stylet is not bent into the proper configuration. Also, the practitioner needs to withdraw the laryngoscope from the patient's oral cavity when the stylet has to be re-shaped, and then re-insert the laryngoscope into the patient's oral cavity followed by the newly-formed stylet and endotracheal tube. Therefore, current conventional medical devices can increase the time needed to intubate the patient and can cause the practitioner to devote considerable effort in order to properly intubate the patient. Therefore, there is a continued need for intubation devices for use by practitioners and clinicians that are highly reliable, relatively easy to use and are able to synchronize visualization of the vocal cords with endotracheal tube placement. The present invention satisfies these and other needs.

SUMMARY OF THE INVENTION

The present invention is directed to an endotracheal intubation device having a steering capability to allow the distal end of the shaft of the device to be moved to an unlimited number of different angular positions to steer the device with its mounted endotracheal tube to a desired target location. The endotracheal device made in accordance with the present invention utilizes a haft of varying rigidity made either from a flexible material like a conventional endoscope requiring a conduit through which it is passed, or which incorporates a malleable material which allows the shaft to be pre-formed to a desired configuration to allow for easier placement of the steerable distal tip in the target location. The steerable distal end tip of the shaft, either with a flexible or malleable shaft proximally, is very deformable and its angular position can be changed by manipulating a simple steering mechanism, herein described, located at the proximal end of the device. Once the shaft is in the configuration, either with a malleable shaft or via a pre-formed conduit, the angular position of the very distal tip can be changed to direct the distal tip to the target location. Visualization and illumination components can be incorporated into the device at the distal end as in a conventional endoscope. For tracheal intubation, the endotracheal tube is mounted co-axially, the vocal cords identified using these components and the tube positioned in the trachea with uninterrupted visualization during its passage.

The endotracheal device of the present invention can be used in conjunction with a novel tongue retractor device which forms a conduit through which the flexibly configured embodiment of the endotracheal intubation device can pass to visualize and position the flexible distal tip of the shaft near the tracheal opening. The present invention acts somewhat like the blade of a conventional laryngoscope by retracting the patient's tongue out of the way to help in positioning the endoscope. The conduit formed by the retractor provides easy passage of the flexibly configured shaft and mounted endotracheal tube into the patient's oral cavity. The tongue retractor includes a handle attached to it that allows the medical practitioner to position it within the patient's oral cavity. The handle allows the practitioner to move the tongue as needed so that the distal end of the conduit is past the tongue, in the retropharynx, near the larynx. Thereafter, the endoscope and overlying endotracheal tube are steered through the vocal cords and into the trachea. The handle can be removably attached to the retractor blade to allow the practitioner to remove the handle, if needed, in order to place an oxygen mask tightly over the patient's mouth without the need to remove the retractor blade from the patient's oral cavity. The retractor thus functions as an airway to enable bag- and -mask ventilation of the lungs.

The present invention can be made as a stand-alone malleable stylet, without visualization ability, having a steerable distal end that could be used with a laryngoscope utilizing direct or indirect visualization. In this embodiment, conventional direct laryngoscopy or indirect fiberoptic endoscopy with a separate monitor is used to visualize the vocal cords. The stand-alone stylet is then used in conjunction with either of these modes of visualization to provide fine control of the distal tip and steer the overlying endotracheal tube through the vocal cords. (It should be noted that with direct or indirect laryngoscopy there is always the possibility of the endotracheal tube itself blocking the view of the vocal cords, whereas endoscopy as here described cannot, since the visualization components are within the tube itself.) The endotracheal device of the present invention can be hermetically sealed allowing the device to be immersed in a sterilizing solution without compromising the components of the device. The tongue retractor of the present invention can be re-sterilized or discarded.

The endoscopic version of the device, which, unlike the stand-alone stylet version, incorporates visualization capability, includes a handle which is cradled by the palm, three fingers, and webbing of the thumb to obtain a firm grip. Then, using the tips of the thumb and index finger, the practitioner can then manually manipulate the steering control mechanism which causes the steerable distal end of the shaft to move to an angular position in alignment with the opening of the trachea. After the distal end of the endotracheal tube has been placed in the trachea, it is held in place with one hand while the endoscopic instrument is removed from the patient's oral cavity with the other hand. The balloon cuff of the endotracheal tube can then be inflated and ventilation of the patient's lungs can begin.

As is mentioned above, the present invention may utilize a malleable shaft which allows the medical practitioner to pre-bend the shaft into a desired configuration. This embodiment allows the practitioner to shape the shaft as needed to achieve a configuration that will extend around the varying anatomical features of the patient, allowing the distal end to be placed near the opening of the trachea. Once the steerable distal end is placed "in the ballpark" of the trachea opening, the practitioner then utilizes the visualization components to identify the vocal cords and then steer the distal end of the shaft with its overlying endotracheal tube through the vocal cords and into the trachea. By moving the distal end to an angular position which aligns the endotracheal tube with the opening of the trachea and advancing toward it, the practitioner then only has to move the endotracheal tube into the opening. In one aspect, the shaft can be made from a malleable tubing. Alternatively, a malleable rod can be inserted into the inner lumen of the shaft to provide the stiffness needed to maintain the shaft in its pre-shaped configuration.

The tongue retractor of the present invention can be made into a curved conduit in various shapes and sizes to accommodate patients of different size and age. Alternatively, the retractor can be made from a malleable material which allows the practitioner to pre-bend it to a desired shape. As is mentioned above, the tongue retractor is attached to a handle by means of which it can be moved while inside the pharynx into different positions. The endoscope can then be advanced through the conduit formed by the retractor, which has moved the tongue out of the way, and identifies the vocal cords and is guided into the trachea. In one aspect of the present invention, the retractor includes an upper shell releasably connected to a lower shell. After the endotracheal tube is placed, the tongue retractor can be removed from the patient. However, if the retractor applies force to the endotracheal tube as it is being removed, it may pull the endotracheal tube out with it. This is certainly undesirable. In the invention described, the retractor can be made from two shells releasably connected together, the retractor can be easily split apart, thereby creating two pieces which can be more easily removed from the patient's oral cavity without applying friction to the endotracheal tube and dislodging it. In another aspect, the two shell halves can be made to slide relative to each other allowing the shell halves to slide apart and separate, yielding two pieces which will not apply force to the endotracheal tube and possibly dislodge it.

In the present invention, both the flexibly configured and the malleably configured endoscopes, and the stand-alone stylet include a steering control mechanism which is housed within an outer casing. In an embodiment of the present invention, the steering control mechanism is connected to at least one control cable which is/are attached to the steering control mechanism and the steerable distal end of the shaft. For simplicity and clarity, the device here described utilizes two "U-shaped" cables, the open end of each "U" being securely attached to the distal, steerable tip, and the curved portion of the "U' reversible secured to the control disc. For convenience, the four segments formed by the two "U"s being placed orthogonally atop each other is herein described as the "cables." It should be appreciated that a number of cable configurations are possible, including but not limited to: three or more individual cables or as few as one circular cable so folded as to be orthogonal at the proximal end and attached reversibly at the control-disc, while the distal bends of the two loops formed can be secured at the distal or steerable tip. By applying pressure to the control disc at the periphery, the disc will tilt, causing one or combination of cables to be pulled, moving the steerable distal end of the shaft into many different angular positions without removing the device from the patient. The steering control mechanism is designed to be manually moved by the practitioner to move the control cables and the distal end to the desired angular position. In one aspect of the invention, the steering control mechanism includes a control mounting-disc component which is pivotally mounted within the outer casing and attached to the control cables. The pulling force exerted on the control cables can be developed by simply placing force on the control mounting disc with the fingertips of the thumb and index to tilt it to any radial configuration. Since the disc can be depressed at any of 360°, so the tip will be likewise positioned. The steering control mechanism of the present invention thus provides a simple mechanism which allows the medical practitioner to quickly steer the distal end of the shaft to the desired angular position.

One of the problems associated with the bending and re-shaping of the shaft is the fact that the control cables are fixed in length and can cause the steerable distal end of the shaft and the control disc to move to an unwanted angular position whenever the shaft is bent from one configuration to another. This results since one or more of the control cables will have a pulling force (tension) exerted on it as the shaft is moved from one bent configuration to another. This pulling force (tension) acting on one or more of the cables will be, in turn, exerted on the distal end of the shaft and the control disc. As a result, while the shaft could be re-shaped to a new configuration, now the distal tip and the control disc have lost much of their adjustment capabilities.

The present invention eliminates this unwanted movement of the distal end of the shaft by preventing or dissipating any tension being applied by the control cables onto the distal tip or the control disc. This is accomplished via a locking and unlocking mechanism. The locking mechanism is associated with the steering control mechanism and allows the cables to become temporarily freed from the steering control mechanism when the shaft is to be bent to a new configuration. The unlocking of the control cables to the steering control mechanism helps to prevent unwanted tension from being placed on one or more of the control cables caused by bending the shaft. After the shaft has been bent to the desired configuration, the locking mechanism can be tightened and returned to the locked position to lock the control cables to the disc component of the steering control mechanism. As a result, the flexible, distal end of the shaft can be maintained in a substantially straight configuration after the shaft has been bent to the desired configuration and the control disc of the steering control mechanism can be centered. The distal end of the shaft can then be placed into any one of the numerous angular positions via the manipulation of the steering control mechanism. Now the medical practitioner can obtain both the desired shape to the bendable shaft without compromising the ability to move the distal end to the desired angular position.

In another aspect of the present invention, the device utilizes at least one control cable with each end of the control cable attached to the distal end of the bendable shaft. A pulling force on a particular cable will cause the distal end to move to a different angular position. Because the distal tip is more deformable and flexible than the shaft, it will preferentially flex more than the shaft. The connection of each end of the control cable to the distal end of the shaft creates a loop or loops which is, in turn, attached to the control disc component of the steering control mechanism of the device. The loop of the control cable can be attached to the control disc and held in place by the locking mechanism. The locking mechanism can be released at any time to allow the position of the loop or loops to be changed so that tension can be released from a portion of the cable whenever the bending shaft is shaped into a desired configuration. The locking mechanism allows the loop(s) of the control cables to be relocked to the steering control mechanism once any developed tension in the control cable(s) has been released.

In one particular aspect of the present invention, the steering control mechanism includes a control mounting disc which can be manually operated to cause the control cables to move the flexible end of the bendable shaft. The user of the device can easily manipulate the control mounting disc to cause the flexible tip of the distal end of the outer shaft to move in omni-directional angular positions to allow the user to steer it into the body cavity of interest. The control mounting disc is designed to receive the loop(s) of the control cable(s) and is adapted to move the control cables when the control mounting disc is moved via a tilting action. A simple locking mechanism, such as a fastener like a screw, can be used to lock the loops to the control mounting disc. In all of the embodiments of the present invention, the steering control mechanism can be encased by a flexible control case made from an elastomeric material which provides a hermetic seal to the steering control mechanism. It also provides a stretchable medium which allows the steering control mechanism to be moved (for example, via a tilting action) within the outer casing. In one aspect of the invention, the control mounting disc may be in a pivoting relationship with a center tube which forms a portion of the device. The control mounting disc can be manipulated by the user's fingers to move the control cables to control the angular deflection of the distal end of the shaft. A biasing member, such as a spring, can be connected to the control mounting disc and a spring support mounted within the outer casing to maintain a bias on the control mounting disc to maintain it in a neutral position.

The endoscopic version of the present invention may include visualization components, such as a video image screen or eyepiece lens, which could be incorporated into the device. The visualization components can be coupled to a power source that can be housed, for example, within the handle of the device. The visualization components may include a fiber optic cable or fiber which extends through the length of the bendable shaft and includes a lens located at the distal end of the shaft. Appropriate coupling components can be utilized to complete the connections of the various visualization components. A light source can extend through the shaft and out of its distal end to provide illumination at the distal end of the shaft.

The present invention can be designed in a number of various sizes and shapes to be used in a number of medical endoscopic procedures, including but not limited to, endotracheal intubation, colonoscopy, bronchoscopy, ureteroscopy, nasal and ear examinations and procedures, and the like. The steering mechanisms of the present invention can be incorporated into instruments which could be used in non-medical situations as well (e.g. as a borescope).

In another aspect of the present invention, a method for placing an endotracheal tube into the trachea of a patient includes placing an endotracheal tube on a device herein described having a shaft with a steerable distal end, the device incorporating a novel steering control mechanism capable of moving the distal end to an unlimited number of different angular positions using only one hand. A conventional endoscope usually has two independent wheels controlling vertical and horizontal movement separately. Two hands must be used to achieve true unlimited radial movement of the distal tip, but that would leave the device itself unsupported. (In practice, the entire device is rotated on the long axis, but this is not the same as true radial capability.) A novel tongue retractor can be placed within the oral cavity of the patient displacing the patient's tongue in order to better visualize the opening to the trachea. Thereafter, the flexible shaft of the endoscope described here and overlying endotracheal tube can be advanced through the conduit formed by the tongue retractor. Once the endoscope has been positioned beyond the base of the tongue and in the vicinity of the vocal cords, these latter structures are searched for and identified. The endoscope is then advanced, utilizing the steering mechanism to always keep the vocal cords in view. Then, at least a portion of the endotracheal tube is advanced through the vocal cords into the trachea. The inflatable balloon cuff of the endotracheal tube could be inflated to seal the endotracheal tube in the trachea, the endoscope removed, and inflation of the lungs can commence immediately via the endotracheal tube, with the conduit still in place. After the patients is adequately ventilated, the tongue retractor could then be removed from the patient's mouth.

These and other advantages of the present invention will become apparent from the following detailed description of preferred embodiments which, taken in conjunction with the drawings illustrate by way of example the principles of the invention.

BRIEF DESCRIPTION OF THE DRAWINGS

FIG. 3A is a perspective view of the embodiment of the tongue retractor shown in FIG. 2.

FIG. 3B is a side perspective view of the handle of the tongue retractor shown in FIG. 3A.

FIG. 3C is a side perspective view of the upper shell which forms a portion of the tongue retractor of FIG. 3A.

FIG. 3D is a perspective view of the lower shell which forms a portion of the tongue retractor of FIG. 3A.

FIG. 4 is a perspective view (with top of outer casing removed) of an embodiment of a stand-alone stylet made in accordance with the present invention having steering capability to control the angular position of the steerable distal end of the bendable shaft of the device.

FIG. 19 is a side elevational of an embodiment of a stylet made in accordance with the present invention with a endotracheal tube extending over the shaft of the instrument.

FIG. 20 is a side elevational along line 20 of FIG. 19 showing the steering control mechanism in an unlocked position.

FIG. 21 is a cross-sectional view of the distal end of the bendable shaft taken along line 21 of FIG. 19.

FIG. 22 is a side elevational of the stylet of FIG. 19 with the malleable shaft shaped to a particular configuration.

FIG. 23 is a side elevational view along line 23 of FIG. 22 showing the proximal end of the stylet with the steering control mechanism in a locked position.

FIG. 24 is a side elevation of the stylet of FIG. 22 with the flexible distal tip steered to another particular angulation.

FIG. 25 is a cross-sectional view along line 25 of FIG. 24 showing the proximal end of the stylet with the steering control mechanism in a locked position.

DETAILED DESCRIPTION OF THE PREFERRED EMBODIMENTS

Figure 1:
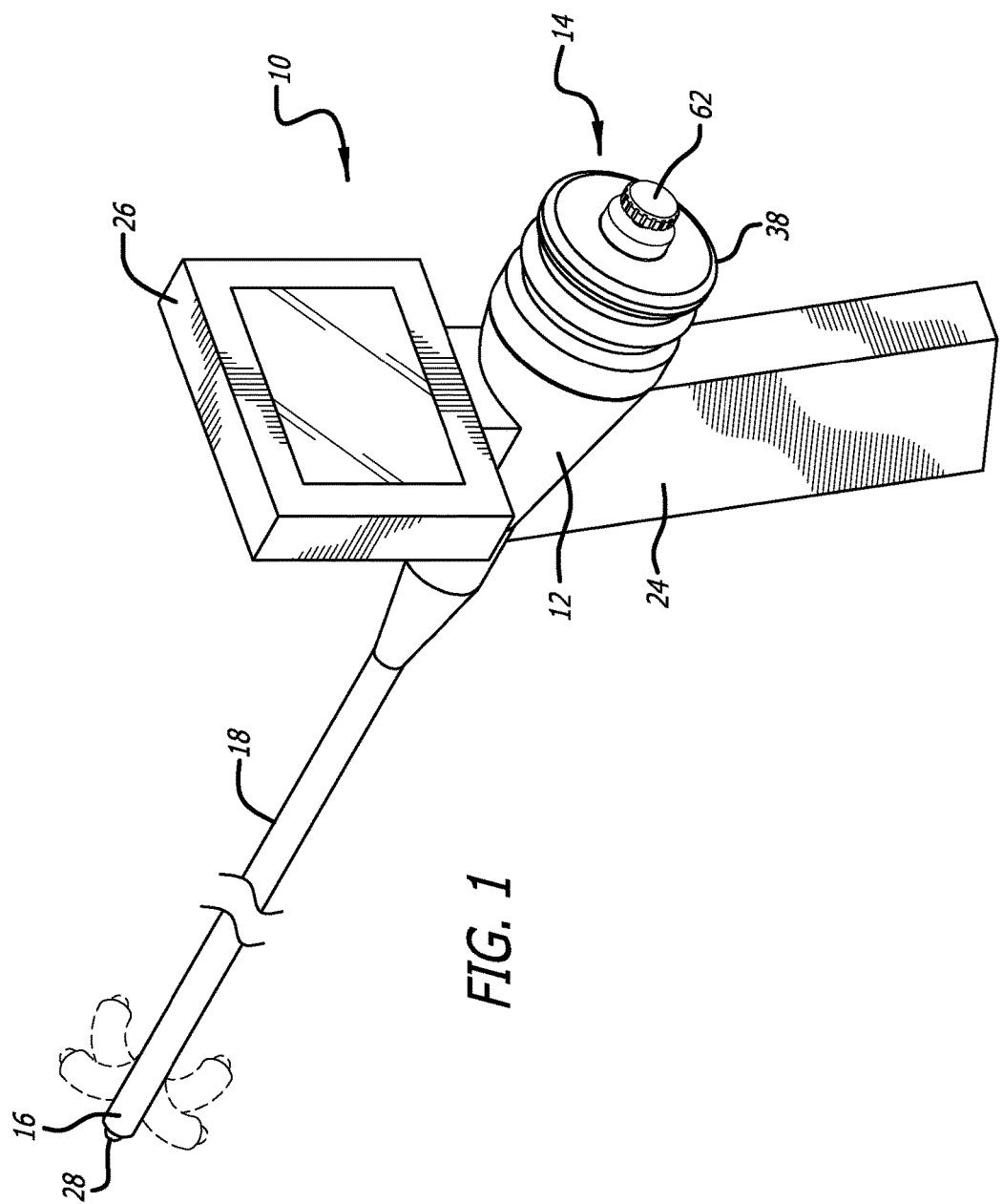
FIG. 1 is a perspective view showing an embodiment of an endoscope made in accordance with the present invention having visualization components along with steering capability to control the angular positions of the steerable distal end of the bendable shaft of the device.
Figure 2:
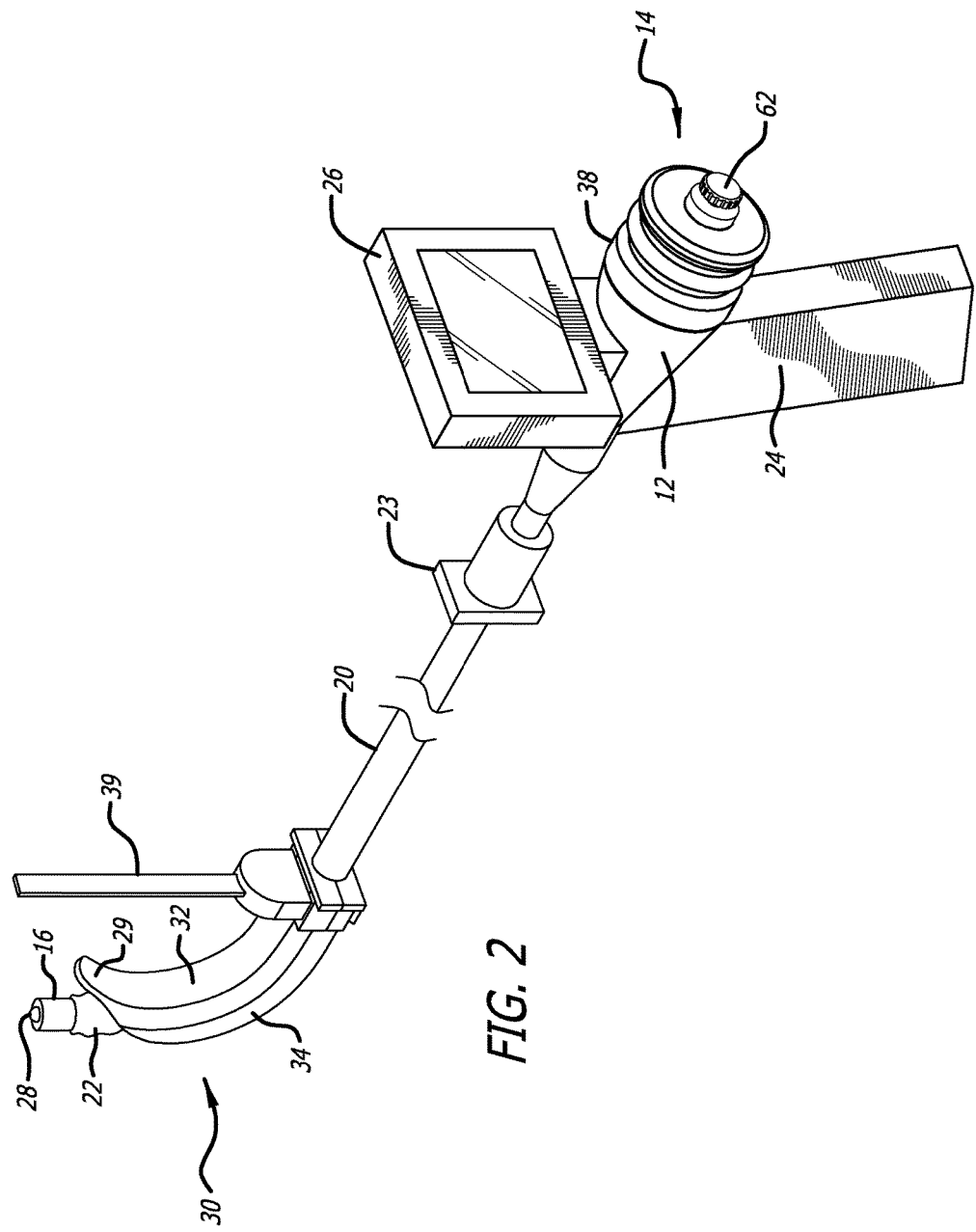
FIG. 2 is a perspective view of the endoscope of FIG. 1 with a endotracheal tube and a tongue retractor mounted on the bendable shaft of the endoscope.

Embodiments of devices made in accordance with the present invention will now be described in detail with reference to the accompanying drawings. Referring initially to FIGS. 1 and 2, a hermetically-sealed endoscope 10 made in accordance with the present invention includes an outer casing 12 which houses a steering control mechanism 14 that can be manually manipulated to steer the distal end 16 of a flexible or malleable shaft 18 to a number of different angular positions. The steerable distal end 16 is shown in its neutral position (where the distal end is substantially straight) which maximizes the number of different angular positions that can be taken achieved. Just a few of the numerous angular positions that can be attained by the distal end 16 are represented by dotted lines appearing in FIG. 1. A removable endotracheal tube 20 (FIG. 2) with an inflatable balloon cuff 22 located at its distal end and a t-piece fitting 23 at its proximal end can be placed co-axially over the flexible or malleable shaft 18 to allow the endotracheal tube 20 to be placed into the opening of the desired body cavity. While the present invention is shown and described as an endoscopic instrument used in a tracheal intubation procedure, it should be appreciated that the present invention can be used in a number of medical procedures and can be adapted in size and shape to fit other body cavities of the patient. Additionally, the present invention in endoscopic form can be used in non-medical applications as well.

The endoscope 10 includes a handle 24 which enable the medical practitioner to firmly grasp the instrument during the medical procedure. The endoscope 10 includes a visualization system incorporated into the device which includes a video monitor or screen 26 mounted on the outer casing 12 just above the handle 24 to provide the practitioner with a clear view of images appearing at the distal end 16 of the flexible or malleable shaft 18. The endoscope 10 includes image transmitting components and light transmitting components for providing illumination at the distal end 16, which are described in greater detail below. As can be seen in FIGS. 1 and 2, a wide angle lens 28 extends from the distal end 16 of the bendable shaft 18. The visualization and illumination components which can be incorporated into the endoscope 10 can extend from the outer casing through an internal lumen of the shaft 18 to the distal end 16. A removable battery pack (not shown) can be placed with the handle 24 to power the visualization and illumination components. Both the video screen 26 and battery pack can be easily removed from the outer casing 12 to allow the unit to be immersed in a sterilizing solution without compromising the steering control mechanism 14 or other visualization components housed within the shaft 18 and outer casing 12. As will be described below in greater detail, the endoscope 10 can be hermetically sealed to protect the internal components from the sterilization solution.

The endoscope 10 includes a number of control cables having segments (shown in FIGS. 4, 10, 12 and 15) which extend from the steering control mechanism 14 to the distal end 16 of the shaft 18. These control cables are described in greater detail below. The steering control mechanism 14 is designed to apply tension to these control cables singly or in combination so that the distal end 16 will move into any one of various angular positions. The practitioner can manipulate the steering control mechanism 14 by simply pushing the components forming the steering control mechanism with her/his fingers to cause the control cables to move resulting in the distal end 16 being bent to the desired angular position.

Referring specifically to FIG. 2, a tongue retractor 30 is shown positioned with the endoscope 10 of FIG. 1. The tongue retractor 30 is designed to extend co-axially over the endotracheal tube 20 and the flexibly-configured shaft 18 of the endoscope 10. As its name implies, the tongue retractor 30 is used to move the patient's tongue out of the way in order to better visualize the vocal cords which comprise the opening of the trachea and are therefore the target of endotracheal intubation. The upper portion of the tongue retractor 30 (the portion which actually contacts the tongue) is somewhat stiff to allow the practitioner to move the tongue during the procedure. The tongue retractor 30 functions somewhat like a laryngoscope in it is used to retract and control the position of the tongue to create a passage for visualizing the vocal cords and placing the tube. The conduit formed by the current device also protects the visualization components from oral secretions that can obscure the view and require removal and cleaning of the device.

The particular embodiment of the tongue retractor 30 of FIG. 2 is shown in greater detail in FIGS. 3A-3D. As can be seen in FIGS. 3A-3D, the tongue retractor 30 includes an upper shell 32 connected to a bottom shell 34. The upper shell 32 and lower shell 34 of the tongue retractor form a lumen (a conduit) through which the flexible shaft 18 of the endoscope 10 and the endotracheal tube 20 may pass through in order to position the distal end of the shaft 18 within the patient. The upper shell 32 acts like the blade of a laryngoscope in that this upper shell 32 contacts and moves the patient's tongue out of the visual field. Both the upper and lower shells 32 and 34 include an outwardly projection finger tab 35 which can be grasped by the practitioner to split the upper and lower shells 32 and 34 from each other. The upper shell 32 includes a pair of grooves 36 which extend along the length of the shell and are adapted to receive a pair of flanged edges 37 formed along the outer edges of the lower shell 34. This structure allows the upper shell 32 to be split from the lower shell 34 once the retractor 30 is to be removed from the patient. A handle 39 is attached to the upper and lower shells 32 and 34 to provide the practitioner with a structure to grasp when placing the tongue retractor into the oral cavity of the patient. Further, this handle 39 allows the operator to displace the tongue of the patient in order to place the distal end of the retractor 30 in the vicinity of the tracheal opening. The handle 39 is removable from the upper and lower shells 32 and 34 to allow the practitioner to tightly place an oxygen mask on the patient, and ventilate if needed during the procedure, while the upper and lower shells 32 and 34 remain in position within the patient's oral cavity.

The upper shell 32 of the retractor can be made from a stiff plastic material which provides sufficient stiffness when retracting the patient's tongue. The upper shell could alternatively be made from a malleable material, such as, but not limited to a malleable aluminum or copper, which would allow the medical practitioner to bend the shell to a desired configuration to conform with the anatomy of the patient. The lower shell 34 can be made from a material which is less stiff and more flexible than the material used to manufacture the upper shell 32. The softness of the lower shell 34 allows the two shells 32 and 34 to be more easily split from each other. Moreover, the groove 36 formed in the harder upper shell 32 would be stiffer and would provide a stronger structure for accepting the softer, mating edge of the lower shell 34. The materials used to form these shells 32 and 34 could also be plastics well known in the medical arts.

The upper shell 32 of the tongue retractor 30 may include a distal positioning member 29 designed to fit within the epiglottic vallecula, the depression formed between the tongue and epiglottis. The epiglottic vallecula is another important reference location used during the intubation of the trachea. The distal positioning member 29 is to be placed as far as possible into the epiglottic vallecula in order to retract the epiglottis and facilitate direct visualization of the vocal cords. The distal positioning member 29 will help to prevent the retractor blade from being pushed distally any further once engaged with the epiglottic vallecula. In this fashion, the tongue retractor will function very much like a laryngoscope. Alternatively, the tongue retractor could be made without this distal positioning member 29. The tongue retractor 30 is shown having a pre-shaped curve which will help match the anatomy of the patient. It should be appreciated that the tongue retractor 30 could be made with any number of different curves and different sizes to match the different anatomies that may be encountered during the medical procedure. Additionally, as is noted above, the upper shell 32 or a portion of the upper shell 32 can be made from a malleable material which provides the physician with the ability to bend the retractor 30 in order to change its curvature, if needed.

The upper and lower shells 32 and 34 of the retractor blade also include openings 31 formed at the proximal end of the shells which receive a pair of arms 33 extending from the end of the handle 39 (see FIG. 3B). These arms 33 are insertable into the openings 31 to attach the handle 39 to the upper and lower shells 32 and 34. Each arm 33 includes an end designed to engage the edge of the lower shell 34 once the end extends out of the opening 31. These ends of the arms 33 are designed to bias outwardly to engage the edge of the lower shell 34 in order to lock the handle 39 in place once the arms 33 are fully extended into the openings 31. The end of each arm can be easily moved inwardly to allow the arms 33 to be removed from the openings 31. The arms 33 help to keep the upper shell 32 and lower shell 34 of the retractor blade together once the arms 33 are placed into the openings 31.

Figure 3F:
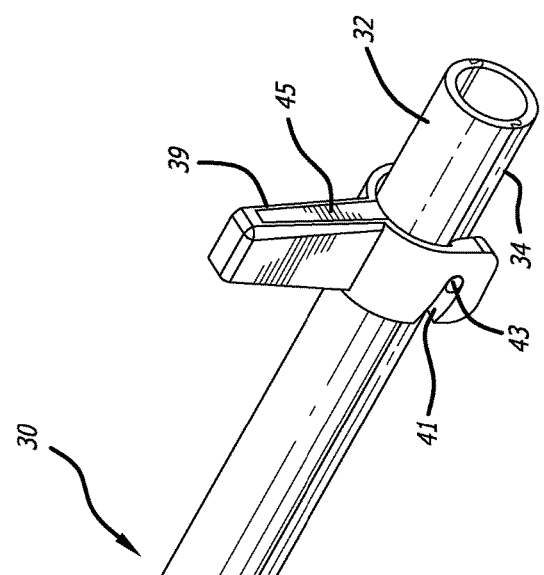
FIG. 3F is a view showing the mating surfaces of the upper shell and lower shell making up the embodiment of FIG. 3E.
Figure 3E:
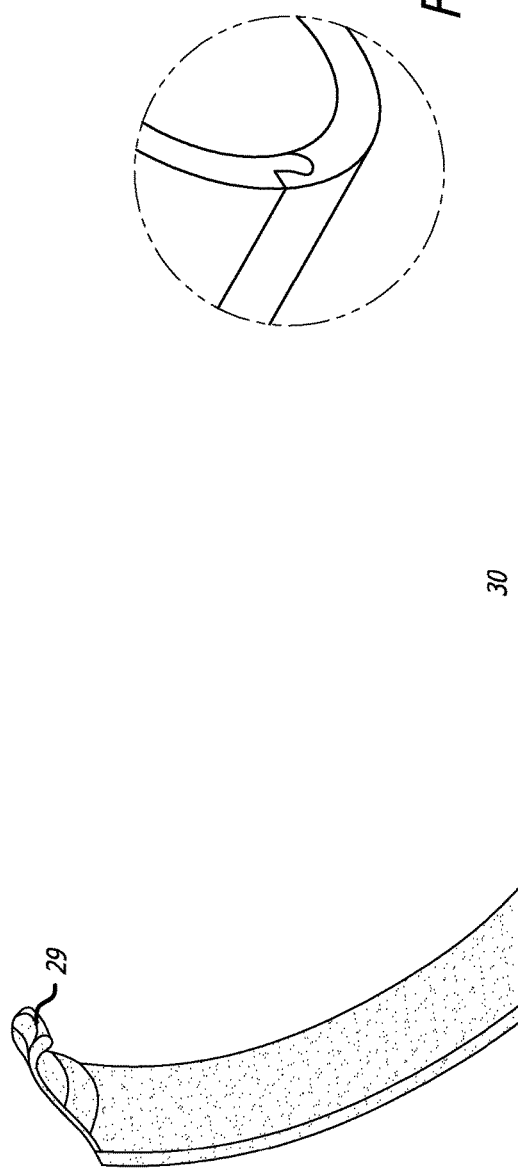
FIG. 3E is a perspective view of another embodiment of a tongue retractor made in accordance with the present invention.
Figure 3G:
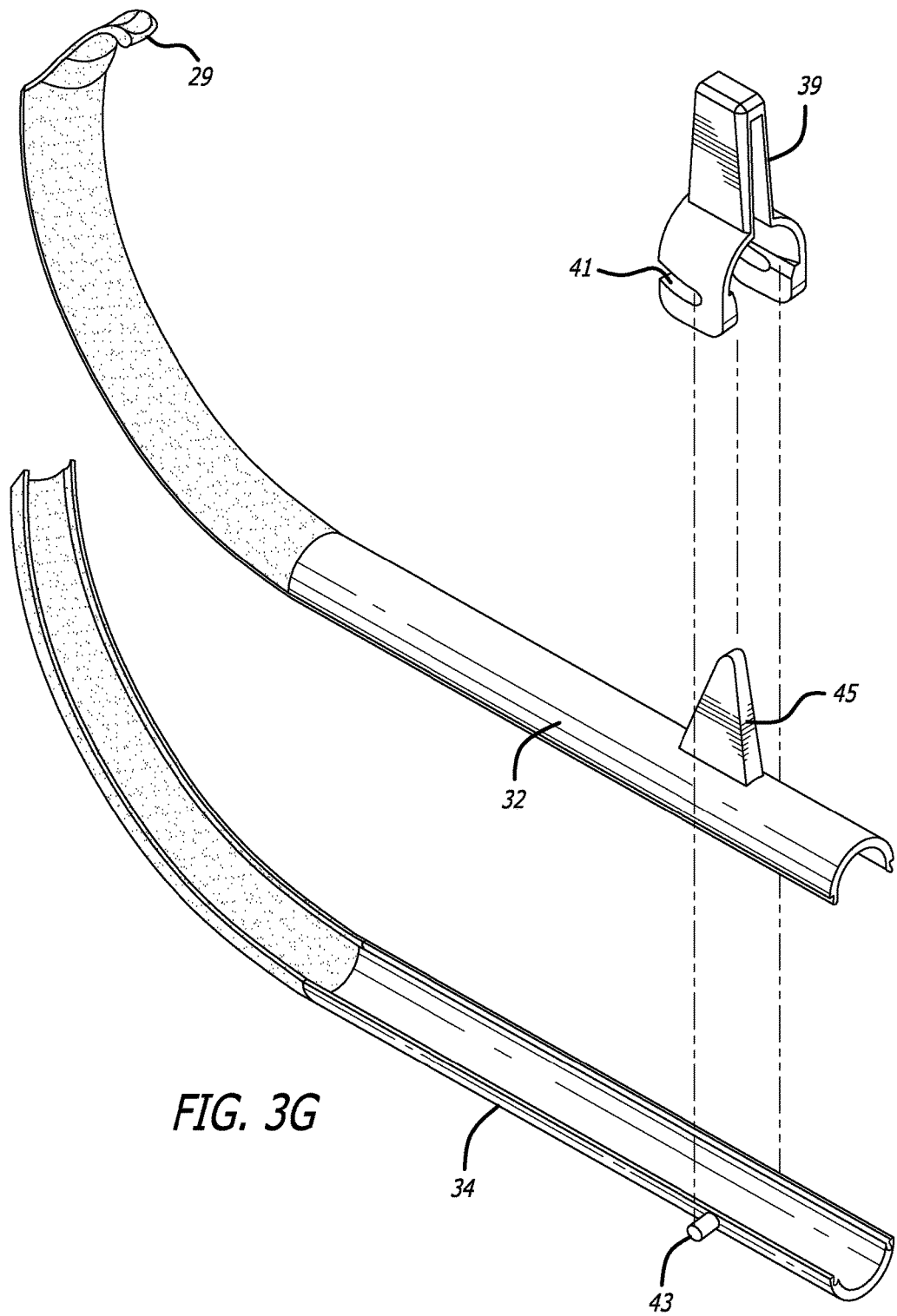
FIG. 3G is a perspective view of the upper shell, lower shell and handle portion which form the tongue retractor of FIG. 3E.
Figure 3H:
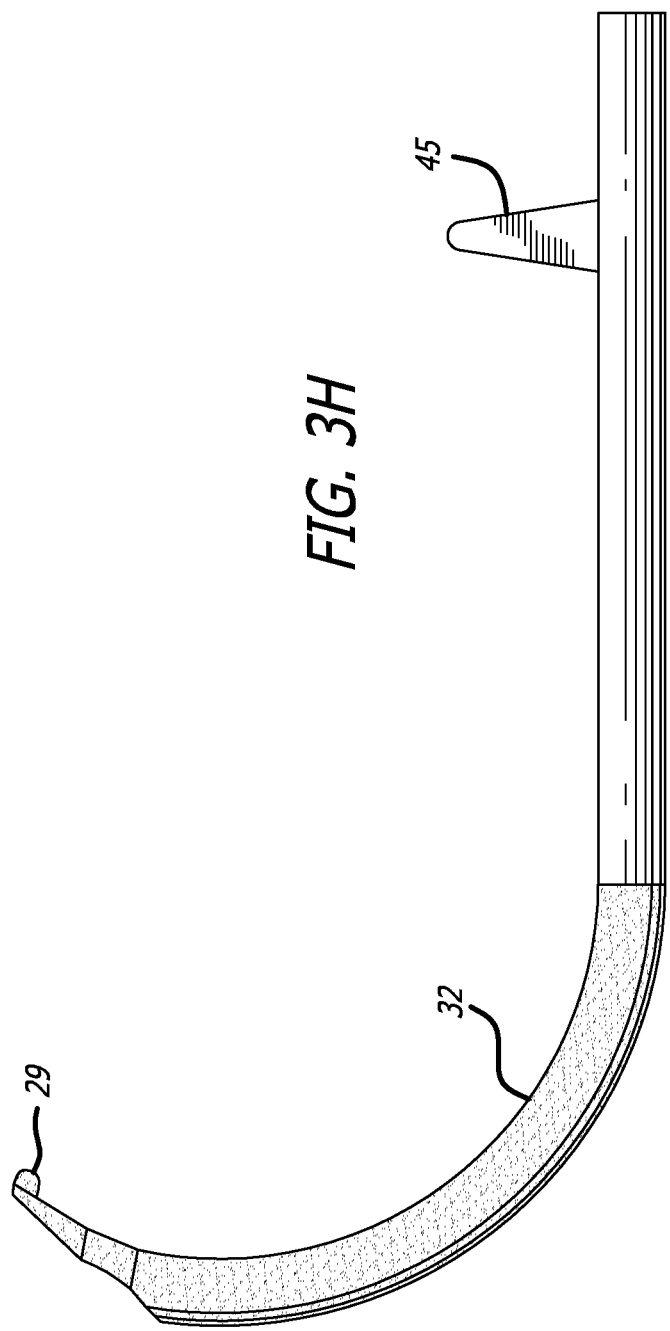
FIG. 3H is a side view of the embodiment of the tongue retractor shown in FIG. 3E.

FIGS. 3E-3H show another embodiment of a tongue retractor 30 which can be used with the present invention. This particular retractor 30 similarly includes retractor blade including an upper shell 32 and lower shell 34. This particular tongue retractor 30 includes a removable handle 39 having a simple release mechanism to easily connect and disconnect the handle 39 to the upper and lower shells 32 and 34. As can be seen in FIGS. 3E and 3G, the handle 39 is shaped with a pair of slotted openings 41 which receive a pin 43 (only one of which is shown in FIG. 3G) formed on the lower shell 34. The handle 39 is designed to extend over an upright support member 45 extending from the upper shell 32. In use, the handle 39 is placed over the upright support member 45 and pivoted to allow the pins 43 to engage the slotted openings 41 to connect the handle 39 to the shells 32 and 34.

FIG. 3F shows the profile of the mating surfaces of upper and lower shells 32 and 34 depicted in FIGS. 3E and 3G which allows the shells 32 and 34 to be peeled away from each other as is discussed above with respect to the embodiment of FIG. 3A-3D. It should be appreciated that there are a number of ways to removably join the upper shell 32 to the lower shell 34. For example, when a malleable material is used to form a portion of the upper shell 32, a tongue and groove joint could be used to help maintain the shells together. Other examples include, but are not limited to, dove tail joints which provide a bit more rigidity to the joint. In some instances, the joint would be more of a sliding type which would require the upper shell to slide relative to the lower shell and split the shells apart. It should again be appreciated that the lower shell 34 or a portion of the lower shell 34 also could be made from a malleable material to allow the tongue retractor to be pre-bent by the operator to a desired shape.

The endoscope 10 made in accordance with the present invention can be hermetically sealed to allow the instrument to be immersed in a sterilizing solution. As can be seen in FIGS. 1 and 2, a flexible control case 38 extends over a portion of the outer casing 12 and is attached to a portion of the steering control mechanism 14. This flexible control case 38 can be made from an elastomeric material which is stretchable to allow the steering control mechanism 14 to be manipulated by the practitioner without impedance but yet provides a barrier to sterilizing solutions. The remaining portions of the endoscope 10 can be manufactured to be hermetically sealed to allow the entire instrument (minus the video screen and battery pack) to be immersed in a sterilizing solution. For example, an elastic sealant may be required to seal any small openings or gaps formed between the visualization and illumination components mounted at the distal end of the shaft. More detailed drawings of this particular embodiment of the control case 38 are provided in FIGS. 5, 10, 16 and 17.

Figure 5:
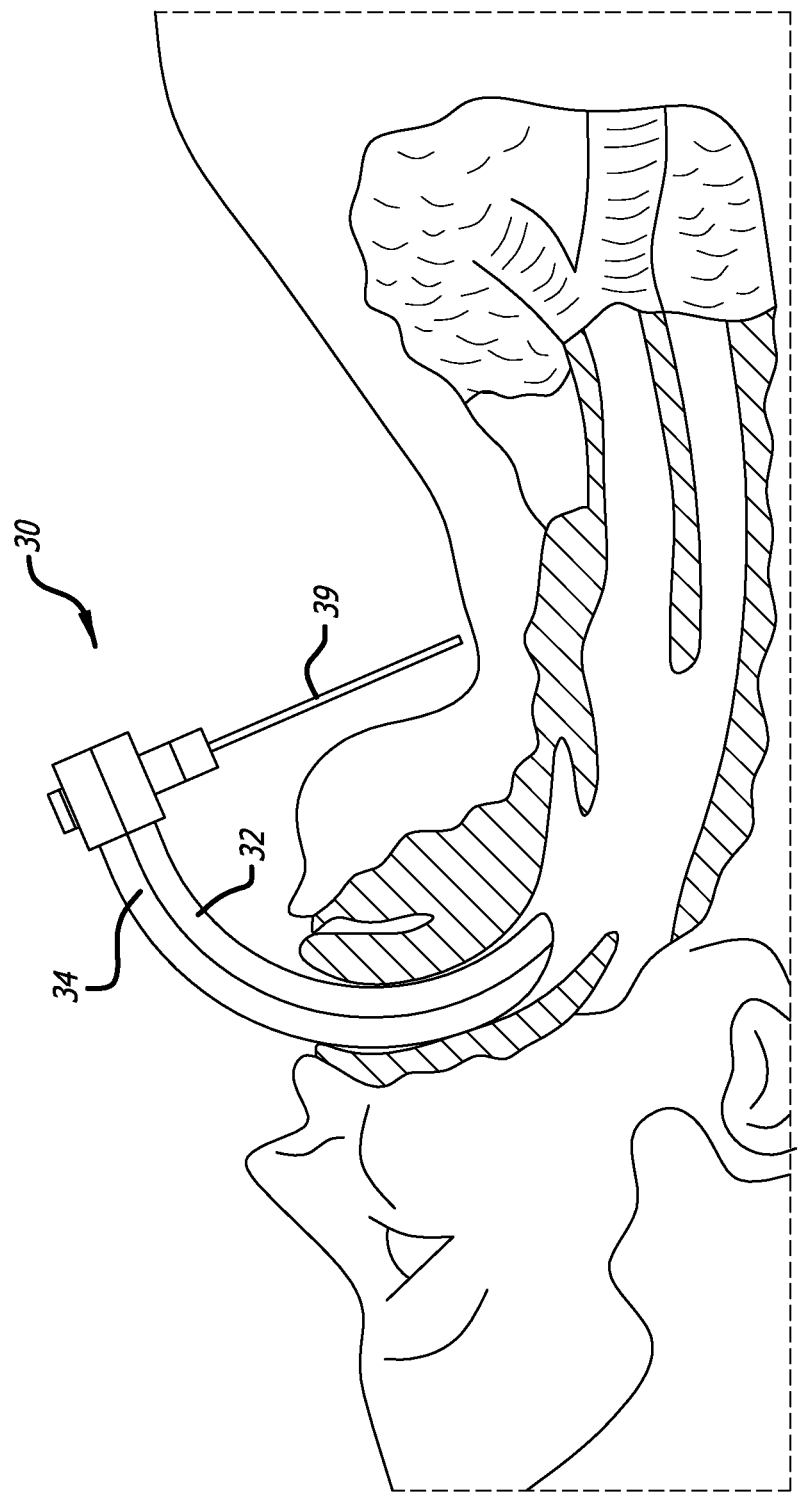
FIG. 5 is a side elevational view, partially in cross-section, showing the tongue retractor of FIG. 2 being steered into the oral cavity of a patient.
Figure 6:
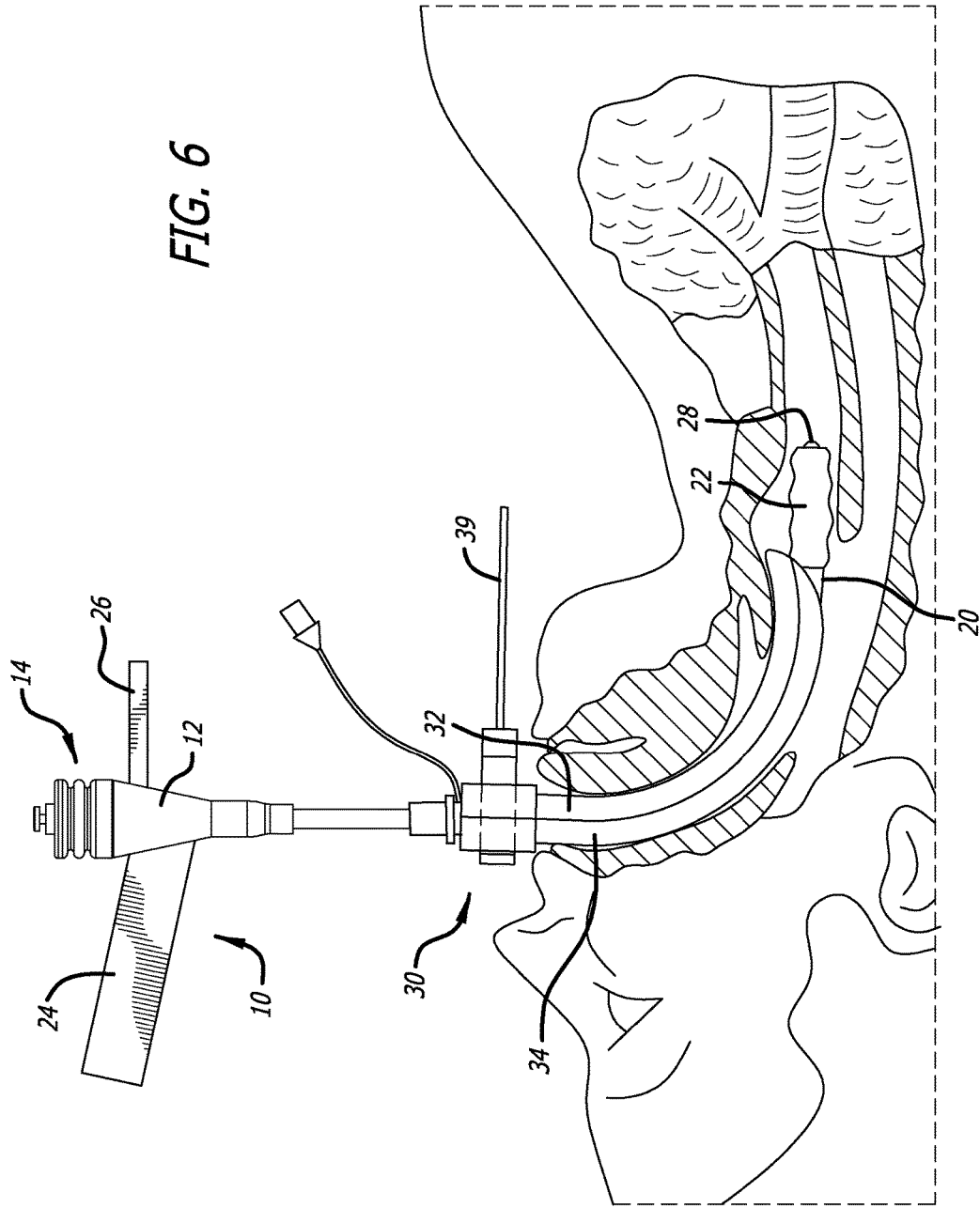
FIG. 6 is a side elevational view, partially in cross-section, showing the endoscope and endotracheal tube of FIG. 2 being steered into the trachea.

FIGS. 5-9 depict how the endoscope 10, endotracheal tube 20 and tongue retractor 30 can be used to perform a tracheal intubation. FIG. 5 shows the tongue retractor 30 being initially inserted into the patient's oral cavity. This tongue retractor 30 moves the patient's tongue and creates a conduit for receiving the remaining components of the system. An upward force can be applied against the tongue by the practitioner so that the tongue will be retracted upwards or sideways to provide better visualization of the vocal cords. Since the tongue retractor is made from a relatively stiff material, it should easily move the tongue and associated tissue. The handle 39 provides a suitable structure which allows the practitioner to apply the necessary force to properly retract the patient's tongue. FIG. 6 shows the composite system consisting of the endoscope 10 with the endotracheal tube 20 co-axially disposed over the bendable shaft 18 of the endoscope being advanced into the patient's trachea. The endotracheal tube 20 is positioned within the lumen formed by the tongue retractor 30 and is steered into place towards the tracheal opening. The visualization and lighting instruments of the endoscope will allow the practitioner to clearly view the location of the vocal cords once the tongue has been retracted. Once the vocal cords are identified, the practitioner can then steer the distal end 16 of the endoscope 10 utilizing the steering control mechanism 14 to allow the practitioner to maneuver the distal end 16 and endotracheal tube 20 into the opening of the trachea, as can be seen in FIG. 6. Alternatively, the practitioner can steer the distal end 16 of the flexible shaft 18 into alignment with the opening of the trachea allowing the endotracheal tube 20 to be positioned directly outside of the trachea opening. The distal end of the endotracheal tube 20 can then be carefully pushed into the trachea. This alternative approach eliminates the need to actually position the distal end 16 of the endoscope into the opening of the trachea. However, absolute confirmation of correct positioning in the trachea is afforded by visualization of the concentric tracheal rings, which lie distal to the vocal cords and are easily distinguished from the interior of the esophagus.

The benefits of the endoscope 10 of the present invention include the ability to steer the distal end 16 of the shaft 18 to any advantageous angular position, allowing the practitioner to simply push the endotracheal tube 20 into the opening of the trachea. The present invention allows the practitioner to utilize a single instrument to advance the endotracheal tube 20 into the trachea thus eliminating the need to manipulate two separate components, such as a laryngoscope and a stylet. In a conventional endoscope both hands are needed to achieve true 360° angular rotation, whereas this is here accomplished by the same hand. It should be appreciated that the malleable shaft 18 can be pre-shaped by the practitioner before it is inverted into the patient's oral cavity or it can be reshaped if the practitioner is having trouble positioning the distal end 16 near the opening of the trachea. The malleability of the shaft 18 thus provides the practitioner with another means by which the device can be manipulated and bent to a desired configuration in order to conform with the particular anatomy of the patient.

Figure 7:
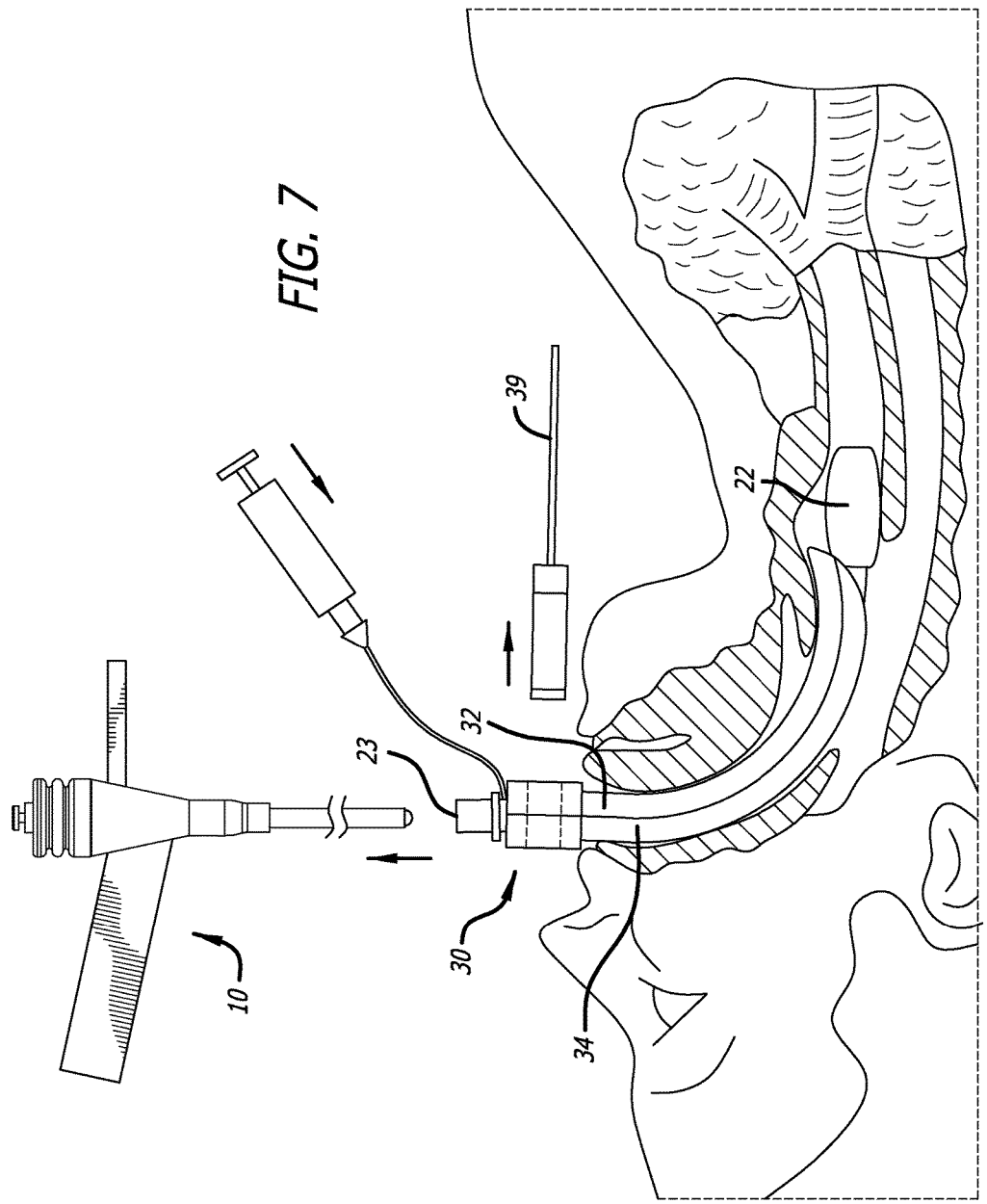
FIG. 7 is a side elevational view, partially in cross section, showing the endoscope of FIG. 2 being removed from the oral cavity of a patient, the balloon cuff of the endotracheal tube being inflated and the handle portion of the tongue retractor being removed from the upper and lower shells.
Figure 8:
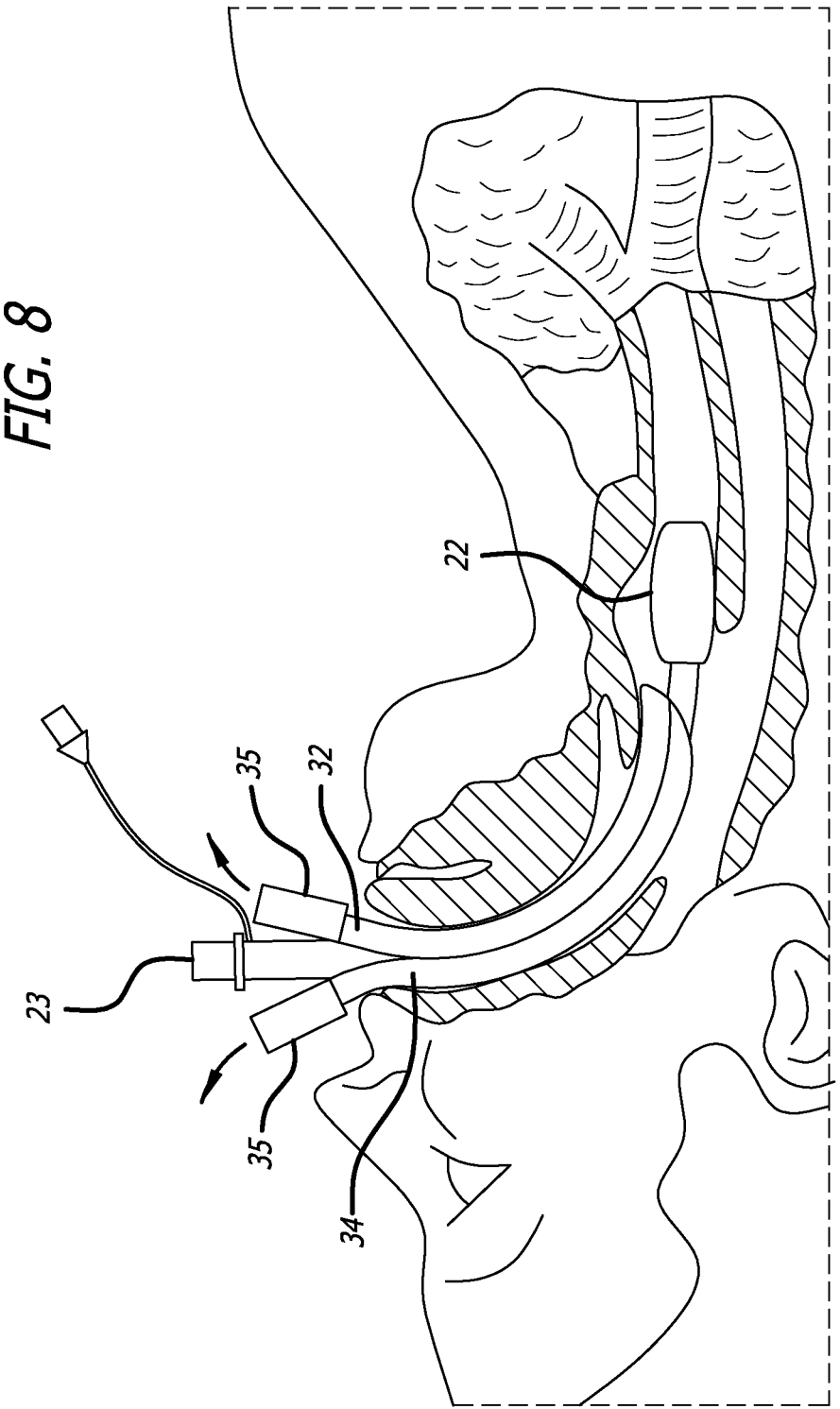
FIG. 8 is a side elevational view, partially in cross section, showing the upper shell and lower shell of the tongue retractor being split from each other in order to remove the tongue retractor from the patient.

FIG. 7 depicts the step of inflating the balloon cuff 22 of the endotracheal tube 20 via syringe 41 which seals the the trachea around the tube. FIG. 7 also depicts the endoscope 10 being withdrawn from the patient's oral cavity leaving only the endotracheal tube 20 and tongue retractor 30 in place. Ventilation of the lungs can be done now with the conduit in place or, after the endoscope 10 has been removed, the handle 39 can be removed from the upper and lower shells 32 and 34, allowing the shells 32 and 34 to be split away from each other and removed from the patient, as is shown in FIG. 8. In use, the finger flanges 35 formed on each of the upper and lower shells 32 and 34 could be grasped with an outward force being applied to each flange 35 to start the splitting action between the upper shell 32 and lower shell 34. Both the upper and lower shells 32 and 34 could be retracted simultaneously from the patient's oral cavity as the splitting action is being applied to the retractor 30 until both shell 32 and 34 are removed from the patient's oral cavity.

In an alternative method, the fitting 22 connected to the proximal end of the endotracheal tube 20 could be removed to allow the tongue retractor 30 to be co-axially retracted from the tube 20. The fitting 22 could be reconnected to the end of the endotracheal tube 20 after the tongue retractor 30 has been removed. In this fashion of removing the tongue retractor 30, there would be no need for a splittable upper and lower shell 32 and 34. Rather, the tongue retractor 30 could be made as a solid piece since the retractor 30 could be simply slide over the endotracheal tube 20 in order to remove it from the patient's oral cavity.

Figure 9:
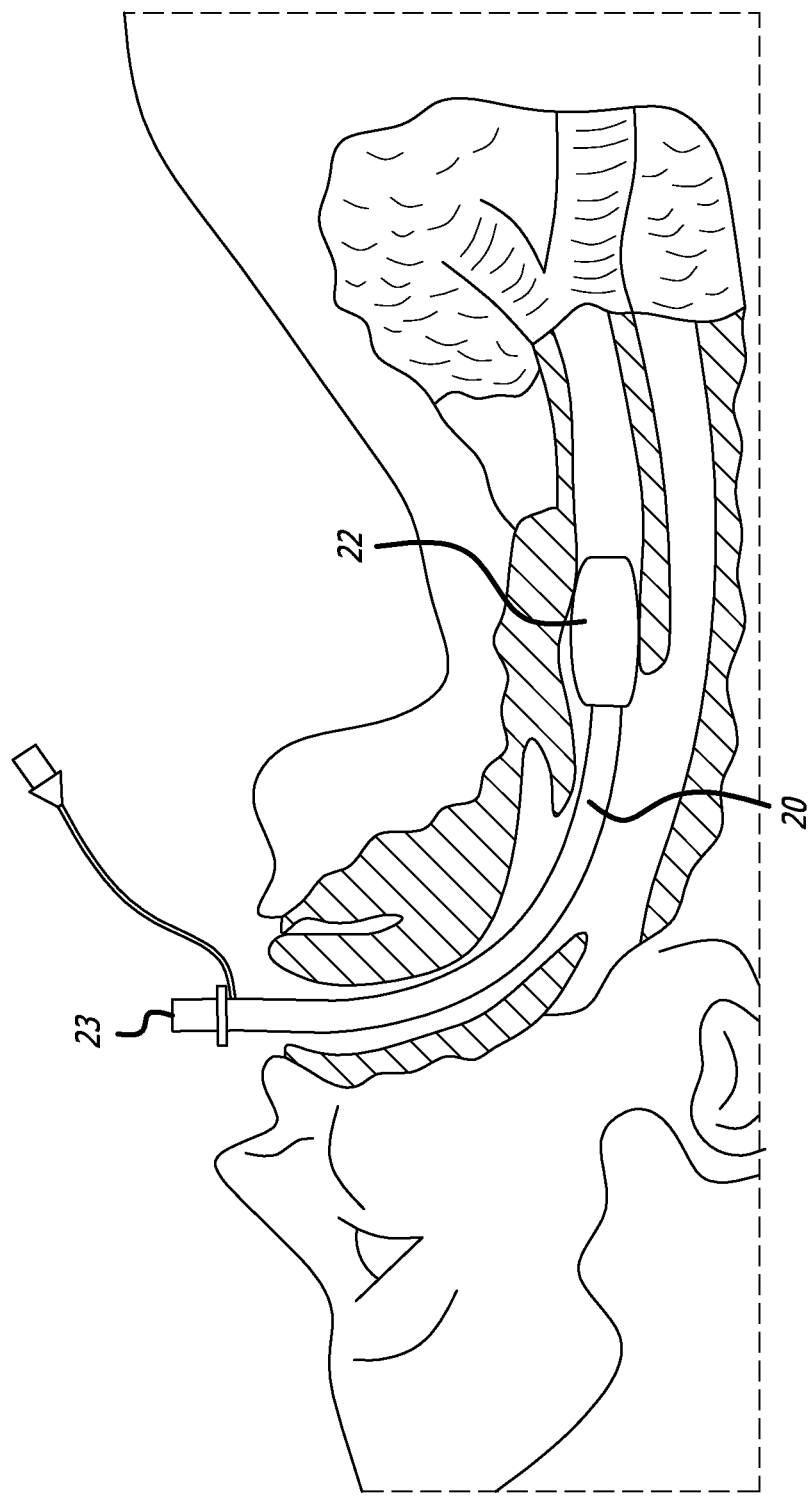
FIG. 9 is a side elevational view, partially in cross-section, showing the endotracheal tube placed within the trachea of the patient.

FIG. 9 shows the endotracheal tube 20 properly positioned in the patient's trachea to maintain an open airway and to serve as a conduit through which certain controlled gases and/or drugs can be administered. If the proximal fitting 23 was removed, it could be placed back on the tube 20. The proximal fitting 23 of the endotracheal tube can then be connected to an anesthesia breathing circuit, bag valve mask device, a mechanical ventilator or other instrument used in the medical procedure.

Another particular embodiment of the present invention is shown in FIG. 4. In this figure, the present invention is shown as a stand-alone stylet 40 which includes many of the same components of the endoscope 10 disclosed in FIGS. 1 and 2. The main differences between the stand-alone stylet version and the endoscopic version of the present invention is the lack of visualization/illumination instruments and a handle in the stylet design. During use, the practitioner can hold the outer casing 12 in order to place the endotracheal tube 20 in place. The stylet could be grasped with the four fingers and palm of the hand and the disc depressed by the thumb in the appropriate location to achieve the desired angulation. Further description of the steering control mechanism 14 appears below in conjunction with the stylet 40 depicted in FIG. 10. The particular stylet 40 shown in FIG. 4 can be utilized, for example, in a conventional intubation procedure in which a laryngoscope is being used. This stylet 40 provides the practitioner with the ability to steer the distal end of the bendable shaft 18 while the stylet 40 is still in the patient's oral cavity. The bendable shaft 18 can also be pre-shaped, as needed, to work around the particular anatomy of the patient.

It should be noted that the stylet 40 may include a side port (shown in FIG. 10) formed in the outer casing 12 which is capable of receiving, for example, the video cable of a visualization system. The video cable and lens could be placed into the internal lumen of the bendable shaft 18 to the distal end 16 of the shaft 18. The video system could thus provide the image appearing at the distal end 16 of the shaft 18 on a remote video screen or monitor.

Figure 10:
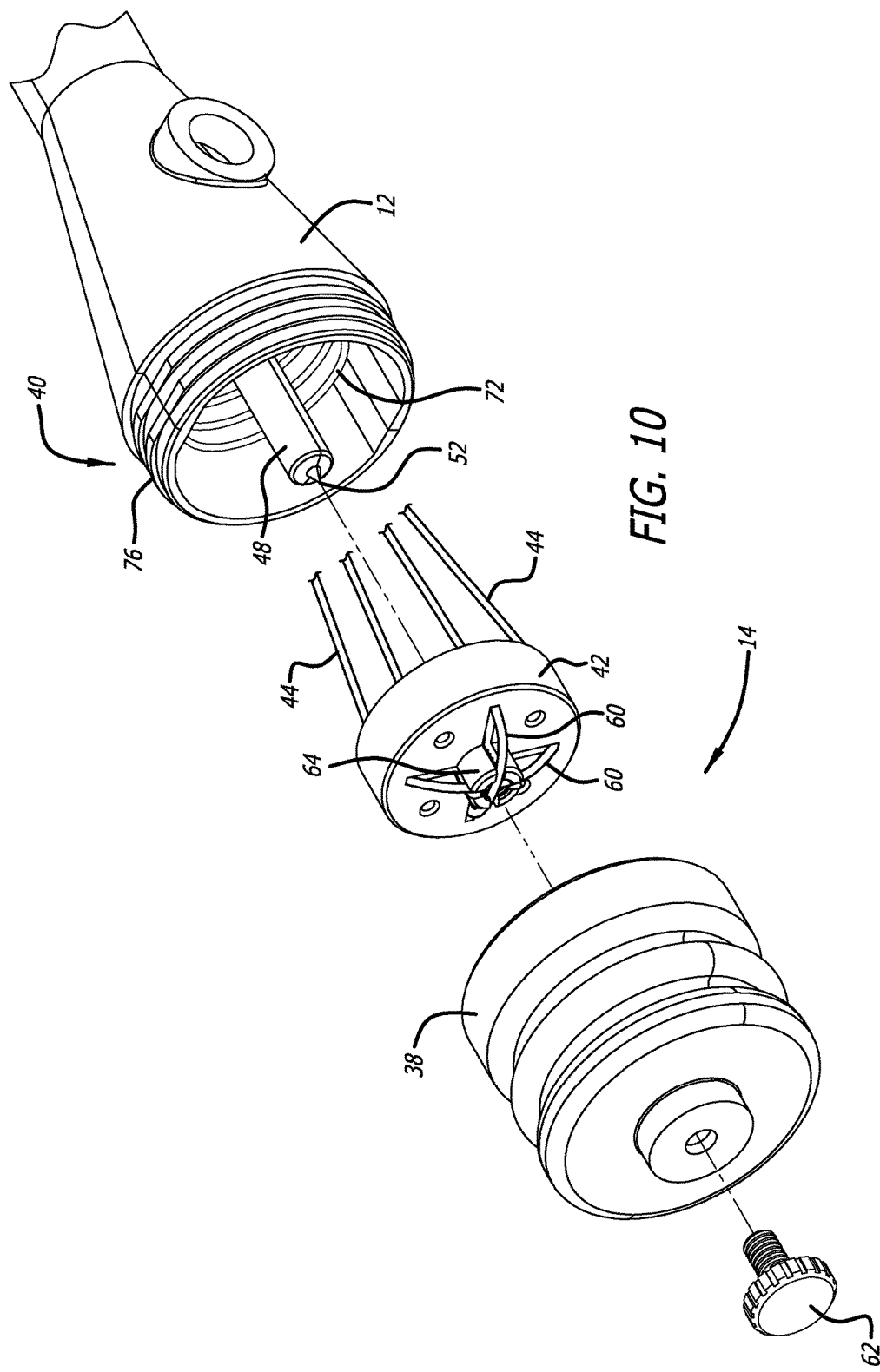
FIG. 10 is a perspective view showing an embodiment of a steering control mechanism and its associated components for steering the distal end of the bendable shaft.

One particular embodiment of a steering control mechanism 14 which can be implemented to steer the distal end of the bendable shaft is disclosed in FIGS. 1, 4 and 10. While the steering control mechanism 14 is shown incorporated into an outer casing 12 used for the stand-alone stylet 40, as shown in FIGS. 4 and 10, this same steering control mechanism 14 can be incorporated into the endoscopic version of the present invention shown in FIGS. 1 and 2. The endoscope 10 of FIGS. 1 and 2 will utilize a different outer casing 12 in order to form the handle 24 and a mount for the video screen 26 but nonetheless can utilize the same steering control mechanism 14 and control cables shown in FIGS. 4 and 10 and disclosed below.

Figure 11:
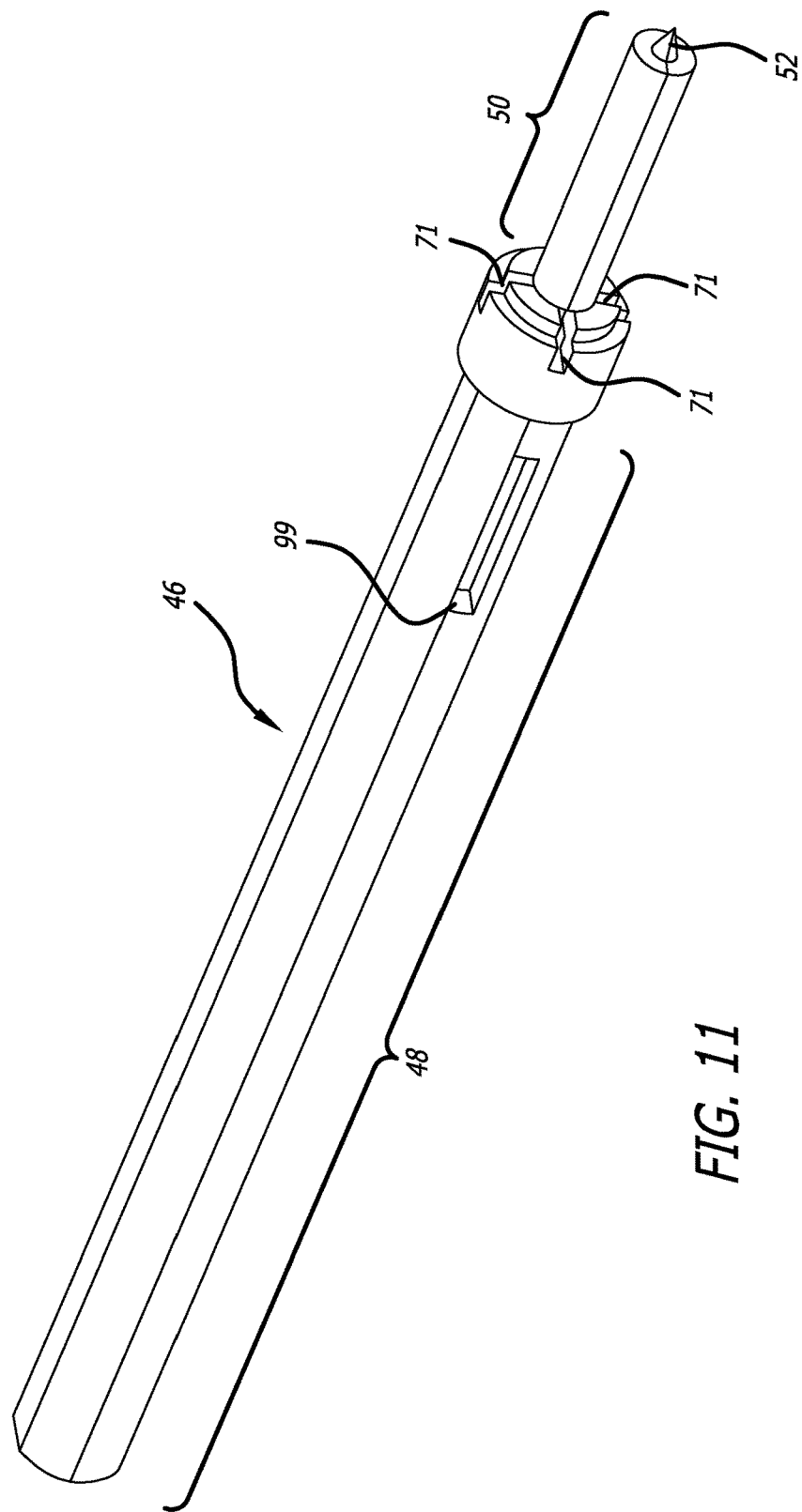
FIG. 11 is a side elevational showing an embodiment of a center tube which forms a apart of the device shown in FIG. 10.

The steering control mechanism 14 (FIGS. 10 and 14) includes a control mounting disc 42 which is connected to the control cables 44 used to move the distal end 16 of the bendable shaft 18. The control mounting disc 42 is housed within the outer casing 12 and is pivotally mounted to a center tube 46 which extends through the outer casing 12. As can best be seen in FIG. 11, the center tube 46 includes a distal portion 48 and a proximal portion 50. The proximal portion 50 is utilized as a pivoting mechanism which allows the control mounting disc 42 to move the control cables 44 to change the angular position of the distal end 16 of the bendable shaft 18. A pivot member 52 (FIG. 14) is located at the end of the proximal portion 50 and is designed to come into contact with a surface formed on the control mounting disc 42. In the particular embodiment disclosed herein, the control mounting disc 42 includes a conically-shaped recess 54 (FIG. 14) which is designed to pivotally engage the pivot member 52 of the center tube 46. In this fashion, the control mounting disc 42 can be pivoted/tilted to any one of a number of different positions to move the control cables 44 and move the distal end 16 to the desired angular position. For example, pressure on the disc at the 12 o'clock position will cause the disc to tilt outwards at the six o'clock position, exerting tension on the cable attached there, causing the distal tip to be deflected downwards. It should be appreciated that the pivot member/conical recess components which allow the control mounting disc 42 to pivot is just one of a number of components which can be used to achieve a pivoting/tilting action. Also, for example, the pivoting member 52 could be formed on the control mounting disc 42 itself with the conical recess formed on the center tube 46. Additional pivoting joints, such as a universal joint, could be used as well to pivotally connect the components together. The pivot itself could be eliminated entirely and the disc be allowed to "float" on the conical spring, with the spring itself forming the pivot. It should be appreciated that the steering control mechanism 14 can utilize any number of different moving mechanism which will allow the practitioner to manually move the steering control disc 42. A pivoting/tilting mechanism is shown for purposes of disclosure.

Figure 12:
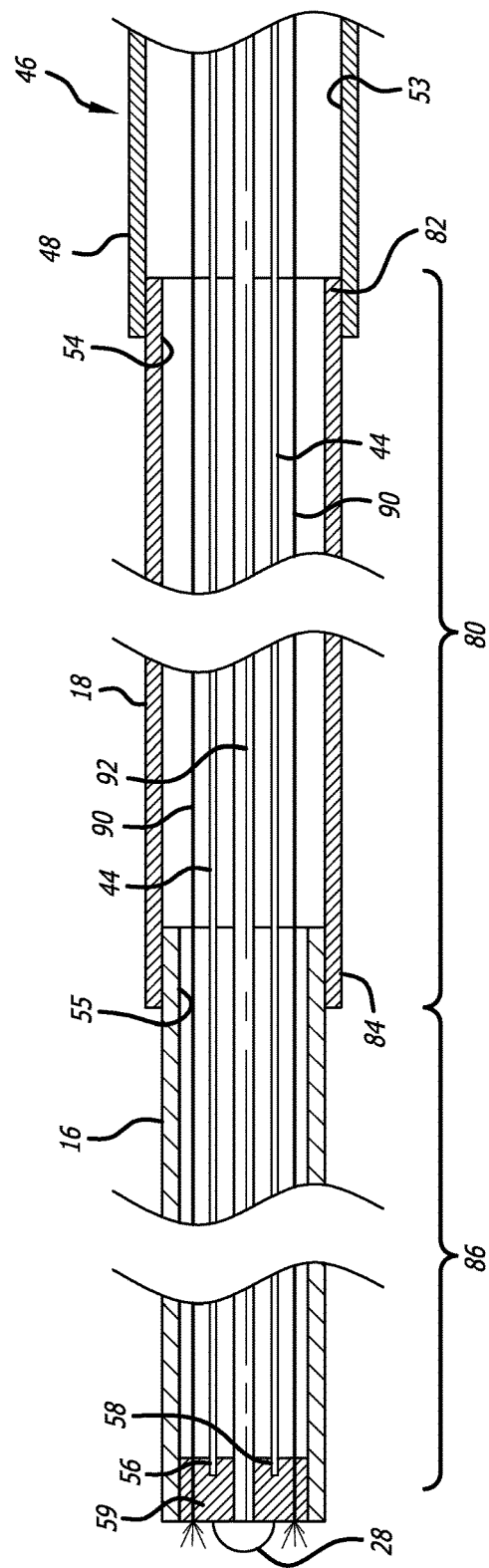
FIG. 12 is a cross-sectional view of an embodiment of a composite bendable shaft made in accordance with the present invention.

The control cables 44 are shown attached to the control mounting disc 42 in FIG. 10. As can be seen in FIG. 12, each control cable 44 extends through the internal lumen 53 of the center tube 46, the internal lumen 54 of the bendable shaft 18 all the way to the internal lumen 55 of the distal end 16. In this particular embodiment of the invention, each control cable 44 includes a first end 56 and a second end 58 which are both connected to the distal end 16 of the bendable shaft 18. Each of the first and second ends 56 and 58 are attached to a plate 59 located at the distal end 16 as is shown in FIG. 12. The ends 56 and 58 of each cable 44 are spaced apart from the other on the plate 59 that the distal end 16 can be moved to a desired angular position whenever the cables 44 are pulled a certain amount. It should be appreciated that another cable configuration could consist of one large closed loop, anchored at the distal tip but allowed to slip through the control disc as it is adjusted and locked in position.

Figure 14:
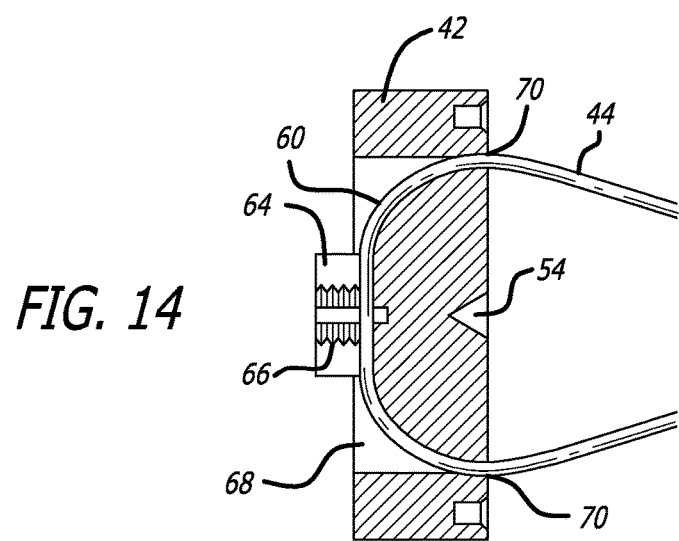
FIG. 14 is a cross-sectional view of an embodiment of a control mounting disc which forms a part of the steering control mechanism.
Figure 15:
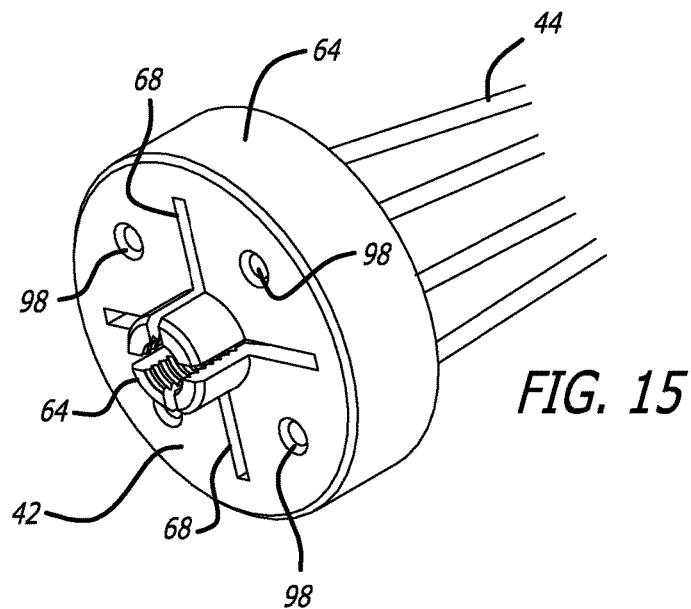
FIG. 15 is a perspective view of an embodiment of a control mounting disc which forms a part of the steering control mechanism.

Since each end of the control cable 44 is attached to the distal end 16 of the shaft 18, a closed loop 60 is formed (FIG. 14) and is connected to the control mounting disc 42. The steering control mechanism 14 includes a locking mechanism which locks each of the loops 60 to the control mounting disc 42. A fastener, such as a compression screw 62, is a simple component which can be used to lock each cable loop 60 to the control mounting disc 42. As can be seen in FIGS. 10, 14 and 15, a mounting structure 64 which includes screw threads 66 can be used to attach and lock the cable loops 60 to the disc 42. The screw threads 66 allow the screw 62 to be screwed downward to contact teach cable loop 60 and lock them in place. The mounting structure 64 (FIG. 14) includes pairs of lateral openings 68 which receive each of the cable loops 60. Openings 70 in the face of the control mounting disc 42 allow the cables 44 to extend through these openings. The control cables 44 then extend though the openings 71 (FIG. 13) which are formed in the proximal portion 48 of the center tube 46 which extend into the internal lumen 53 of the center tube 46 (FIG. 12). In this manner, the mounting structure 64 maintains the cable loops 60 disposed within the lateral openings 68 to center the loops and prevent them from moving in a lateral fashion relative to the control mounting disc 42. Each loop 60, however, can move through the openings 70 until the loop 60 is locked in place by the screw 62. In use, the user merely screws the screw 62 down until it presses the loop 60 against a face of the control mounting disc 42. The loop 60 can be unlocked by simply rotating the screw to releasing the force being exerted on the loop 60 by the screw 62. As can be seen in FIGS. 10 and 15, the loops 60 of the control cables cross each other near the center of the control mounting disc 42 to allow a single screw 62 to lock the loops 60 in place. It should be appreciated that each loop 60 of each control cable 44 could be individually locked by a suitable locking mechanism as well without departing from the spirit and scope of the present invention.

The control mounting disc 42 pivots/tilts about the pivot member 52 formed on the center tube 46 (see FIG. 25). A biasing member, such as a spring 72, (see FIG. 4) is mounted within the outer casing 12 and comes in contact with the bottom face of the control mounting disc 42. The other end of the spring 72 contacts a spring mount (FIG. 4) mounted within the interior of the outer casing 12. The spring 72 provides a biasing force on the control mounting disc 42 to move the disc 42 to its neutral position, as is shown in FIG. 4, whenever there are no forces acting on the control disc 42. Accordingly, when the practitioner removes his/her fingers from the control mounting disc 42, the spring 72 will move the disc 42 back to its neutral position. Whenever the practitioner pushes the control mounting disc 42 in a certain manner, the control cables 44 will either be pulled or relieved of tension to cause the distal end 16 to be moved to a particular angular position. The control cables 44 thus cooperate with each other to achieve the desired angular positioning of the distal end 16.

As can be seen in FIGS. 1, 2 and 4, the steering control disc 42 is encased by the control case 38 which helps to maintain a hermetic seal to the outer casing 12. This control case 38 can be made from an elastomeric material and may be bonded to the outer edges 76 of the casing 12. This cover 38 is designed to come into contact with the control mounting disc 42 to allow the control mounting disc 42 to freely articulate on its pivot member 52 while still providing a hermetic seal. Further details relating to the structure of the particular control case 38 shown in the drawings are disclosed in FIGS. 15 and 16 and are discussed below. The control case 38 may include, for example, grooves 78 formed therein for receiving and holding the edges of the control mounting disc 42. This control case 38 is designed to bend and stretch as may be necessary in order to allow the control mounting disc 42 to freely pivot within the interior of the outer casing 12.

FIG. 12 show a particular embodiment of the shaft 18 and its distal end 16. As can be seen in FIG. 12, the shaft 18 is attached to the distal portion 48 of the center tube 46 and extends to a short length of flexible tubing which forms the distal end 16 of the shaft 18. The shaft 18 can be made from a length of malleable tubing 80 which possess sufficient bending strength to maintain a pre-shaped configuration. The shaft can also be as flexible as a conventional endo-scope, and conform passively to a conduit, whether it be a biological or artificial one. For example, the shaft 18 can be made from a malleable aluminum similar to the malleable aluminum material used in intubating stylets such as those sold and manufactured by Legend Medical Devices of South El Monte, Calif. Other similar malleable materials, such as copper, could also be used. The physical properties of the malleable material allow the practitioner to bend the shaft to a desired configuration without the need to apply excessive force. The malleable material should be strong enough to maintain the configuration in the absence of a strong applied pressure. The proximal end 82 of the malleable tubing 80 is attached to the distal portion 48 of the center tube 46. The distal end 84 of the malleable tubing 80 is, in turn, attached to the easily deformable tubing 86 which forms the distal end 16 of the shaft 18. A helical spring may be used to add flexibility and a biasing element to the distal tip. Suitable and known ways of bonding the tubing together can be implemented. The flexible tubing 86 has a mounting plate 59 which extends within the lumen 55 of the tubing 86. As was mentioned above, this mounting plate 59 is connected to the ends 56 and 58 of the control cables 44. Also, the mounting plate 59 includes openings for receiving optic fibers 90 which extend out of the plate 59 in order to provide illumination at the distal end 16 of the shaft 18. A lens 28, which can be of the wide-angle or "fish-eye" type, extends from the mounting plate 59 as well and is connected to an optic cable 92 which extends through the lumen 54 of the shaft 18 into the outer casing 12 where it is connected to the video monitor 26. The optic fibers 90 and optical cable 92 also extend through the lumen 53 of the center tube 46 and are attached to the power source. The distal end of each optic fiber includes a lens 100 (see FIG. 4) which provides illumination at the distal end 16 of the shaft 18.

Figure 13:
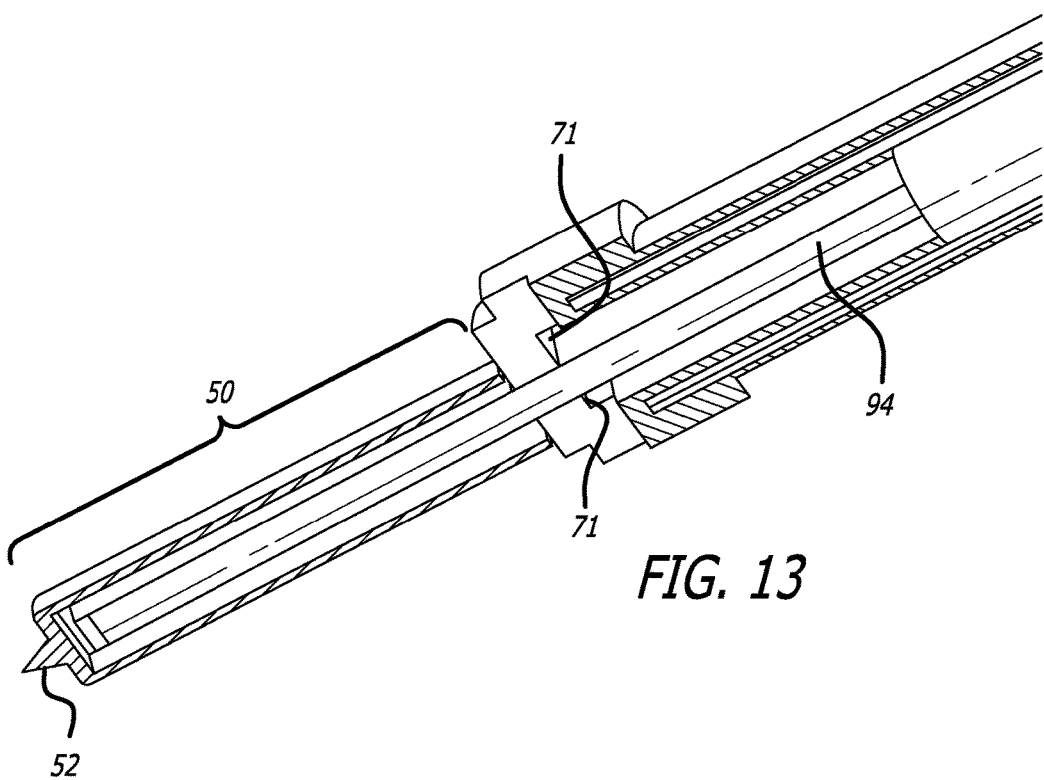
FIG. 13 is another cross-sectional view of an embodiment of a center tube made in accordance with the present invention.

FIG. 13 shows an embodiment of the present invention in which the stand-alone stylet 40 utilizes a malleable rod 94 which extends through the center tube 46 and through the lumen of the bendable shaft. This malleable rod can be connected to the center tube 46 and can extend at least partially along the length of the shaft. In this particular embodiment, a deformable tubing can be used to form the shaft with the malleable rod providing the bendability and strength needed to maintain the pre-shaped configuration. In this manner, the rod and deformable tubing cooperate to obtain the properties needed for the malleable shaft.

Referring now to FIGS. 4, 10 and 14-18, various components forming the embodiment of the stylet and endoscope are shown in greater detail and are further described. FIGS. 14 and 15 show further details of particular embodiment of the control mounting disc 42 shown in FIGS. 4 and 9. As can best be seen in FIG. 15, the cross openings 68 which extend into the face of the disc 42 create abutments which prevent each loop 60 from moving laterally on the disc 42. The mounting structure 64 is shown in FIG. 15 as being cut into four separate sections but is still capable of receiving the screw 62 which tightens down on each of the loops 60 to lock the loops 60 to the disc 42. The conically-shaped recess 54 which pivots on the pivot member 52 of the center tube 46 can best be seen in FIG. 14. The face of the control mounting disc 42 includes openings 98 which are adapted to receive projections 100 formed on the inner surface of the control case 38 (see FIG. 17).

Figure 16:
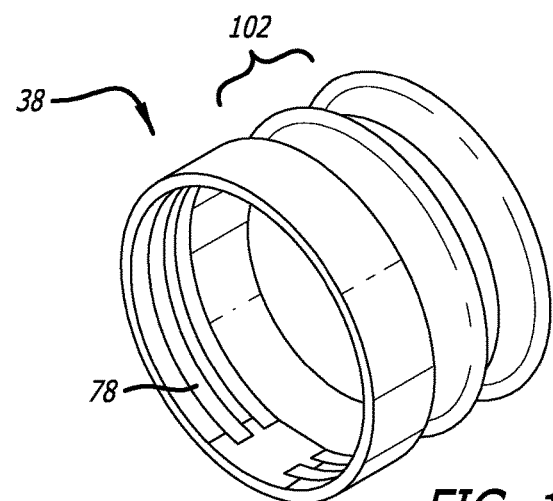
FIG. 16 is a perspective view of an embodiment of a control case which forms a part of the steering control.
Figure 17:
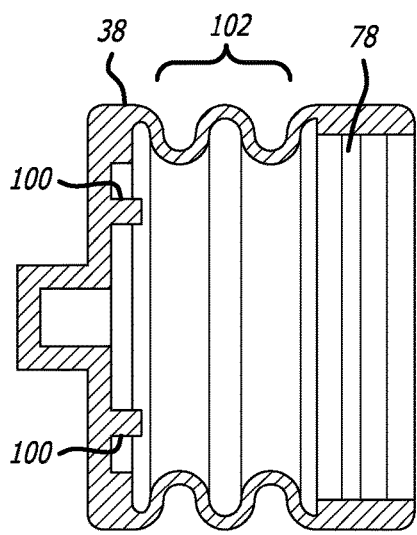
FIG. 17 is a cross-sectional view of the control case of FIG. 16.

The control case 38 is shown in greater detail in FIGS. 16 and 17. FIG. 16 shows the grooves 76 which are designed to engage the structure on the outer edge of the casing 12 (see FIG. 10). The particular control case 38 of FIGS. 16 and 17 show a region where a bellows structure 102 is formed to allow the control case 38 to flex and bend when the control mounting disc 42 is being manipulated by the user. The projections 100 formed on the inner surface of the control case 38 are designed to be placed within the openings 98 formed on the control mounting disc 42. These projections 100 can be bonded within these openings 98 to ensure that the control case 38 remains connected to the control mounting disc 42. The connection of these projections 100 into the openings 98 on the disc 42 also helps to prevent the disc 42 from possibly rotating on the pivot member 52. The remaining portions of the control case 38 could likewise be bonded to the casing 12 to create and maintain the instrument hermetically sealed. A suitable elastomeric material can be used to form the control case 38.

Figure 18:
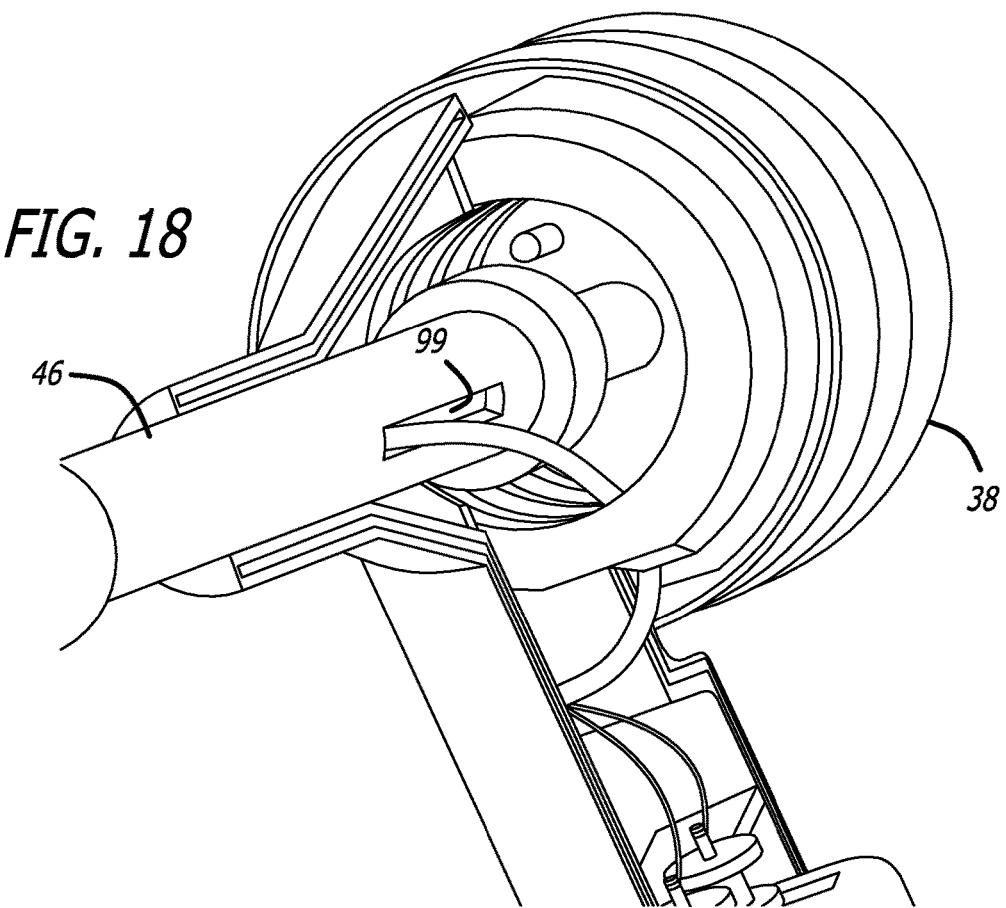
FIG. 18 is a perspective view with a portion of the outer casing removed showing the endoscopic version of the present invention with its handle portion and the cables extending into the lumen of the center tube.

FIG. 18 shows a view of the handle portion of the endoscope 10 of FIGS. 1 and 2 with a portion of the handle removed to show how a battery pack could be placed within the handle 24 in order to provide a portable power source to the visualization and illumination components incorporated into the endoscope. The view also shows a side opening 99 in the center tube 46 which leads to the lumen 53 of the center tube 46 and the lumen 54 of the shaft 18. As can be seen in FIG. 18, a cable is shown entering the side opening 99 in the center tube 46.

The inner lumens of the shaft 18 and center tube 46 may include spacers (not shown) which are basically flat disks (like the mounting plate 59) having openings for receiving the various cables and optic fibers used in conjunction with the endoscope/stylet of the present invention. Such spacers could be placed along the length of the shaft 18 and center tube 46 to help prevent the various cables and optical fibers from tangling with each other during usage.

FIGS. 19-25 depict the benefits of the present invention in utilizing a mechanism which allows the control cables 44 to be "reset" after the flexible or malleable portion of the shaft 18 has been bent to a new configuration. One of the problems associated with prior art devices which utilize control cables or wires to move the distal end of the shaft is the fact that the control wires can have unwanted tension applied to one or more of them whenever the shaft is bent to a new configuration. This occurs if the tension applied to the control cables is changed passively by the bending of the shaft, causing the control cable to move the control disc or the distal tip to an undesired angular position. The present invention is designed to eliminate the possibility that the bending of the bendable shaft will have any impact on the control cables and disc.

The steering control mechanism 14 of the present invention utilizes loops 60 formed by each of the control wire 44 which allows the attachment point of the loops 44 to the control mounting disc 42 be reset after the shaft 18 has been bent to a new configuration. FIG. 19 shows the bendable shaft 18 in a substantially straight configuration (first configuration). The endotracheal tube 20 with its inflatable balloon cuff 22 extends over a portion of the shaft and is shown in these figures covering the steerable distal end of the shaft 18. Since the endotracheal tube 20 is flexible, the steerable distal end still is capable of changing angular position when the steering control mechanism is manipulated. Alternatively, the endotracheal tube 20 could be placed further up the shaft 18 so that the steerable distal end would be fully or partial exposed during usage. As can be seen in FIG. 20, the locking mechanism of the device, namely the screw 62, is in its unlocked position. In this position, the control cables 44 and the loops 60 formed by each of the control cable 44 are free to move. The biasing member, namely the spring (not shown in FIG. 20), provides a biasing force which keeps the control mounting disc in its neutral position, as is depicted in FIG. 20. When the shaft 18 is in its first configuration, the angular position of the distal end 16 of the shaft is substantially straight (its neutral position). This substantially straight or neutral position of the distal end maximizes the number of angular positions to which the distal end can be steered by the steering control mechanism.

When the shaft 18 is in its first configuration, as is shown in FIG. 19, the lengths of each control cable (the length being defined as its point of attachment to the distal end to its point of attachment to the steering control mechanism) are set. These control cables have an initial length when the shaft is in its first configuration.

FIG. 22 shows the same stylet 40 of FIG. 19 except that the shaft 18 has now been pre-bent to a curved configuration (a second configuration). Accordingly, if the loops 60 of the control cables 44 were initially in the locked position on the control mounting disc and the shaft 18 was then bent, there would be tension draw on some of the control cables, which would then act on the distal end resulting in the distal end being moved from its substantially straight (neutral) position to an unwanted angular position. Generally, the control cables on the outside radius of the shaft bend will have additional tension placed on them as opposed to any control cables located on the inside radius of shaft bend. Since the distal end is flexible, any tension acting on the control cable will be applied to the distal end 16 since it is easily susceptible to such forces. Such tension will also be applied to the control disc 42 as well and displace it from its original neutral position. In the drawing of FIG. 23, however, the locking mechanism has remained in the unlocked position as the shaft 18 was bent to its second configuration. Since the loops 60 were unlocked at the steering control mechanism, they are able to move freely, eliminating unwanted tension being applied to the control cables or the disc itself. What in fact happened is that one segment of the control cable has compensated for the increase or decrease in length of the other segment when it is bent from its straight or neutral position. Accordingly, since the relative length of one or more of the cable segments has changed, there is a release of tension on that particular cable that would otherwise act on the distal end 16 of the shaft or the control disc. Accordingly, the change of the relative lengths of the control cable segments from their initial lengths allow the distal end 16 to remain in its desired substantially straight (neutral) position, as is depicted in FIG. 22. Likewise, the control disc 42 will now be returned to or remain in its initial, neutral position, allowing full functionality to further control the distal tip 16. One can easily appreciate that if there was no such mechanism to return the device to a neutral position, functionality would be lost. For example, if the shaft were bent downward, towards six o'clock, tension would be applied to the cables on the outside of the curve, in this instance, the cables on the upward or twelve o'clock side of the shaft, causing the distal tip to bend upward, towards twelve o'clock and the disc would passively react by tilting inward at twelve o'clock and outward at six o'clock. Full ability to tilt the disc and control the distal tip would then be impaired. But if the cable segments are first freed up at the disc, the shaft configured as desired, then the cable segments locked at the disc, full functionality can be maintained. It is only after the shaft 18 is bent into the desired second configuration that the loops 60 should be locked by the locking mechanism to the control mounting disc 42. The resulting structure allows the shaft 18 to be bent to any one of a number of configurations in order to adapt to varying anatomical features of each patient without changing the substantial straight (neutral) position of the distal end.

The angular position of the distal end 16 of the device shown in FIG. 22 can now be easily changed. FIG. 24 shows how the shaft 18 remains in its bent configuration, as is shown in FIG. 22, with the loops 60 remaining in the locked position. The practitioner now simply has to manipulate the mounting disc 42 to change the angular position of the distal end 16 in order to steer the device into the desired position. As can be seen in FIG. 25, movement of the mounting disc 42 (inward at 12 o'clock and outward at 6 o'clock) will cause a tensioning force to be applied to one or more of the control cables 44 which, in turn, causes those control cables to move the distal end 16 from its initial position shown in FIG. 22 (shown in dotted lines in FIG. 24) to its new angular position shown in solid lines in FIG. 24. The arrow in FIG. 24 shows the direction in which the distal tip 16 moves from its initial position shown in FIG. 22 (dotted lines) to its new angular position epicted in FIG. 24 (solid lines).

If there were no compensating device employed, i.e., if the cables were fixed to the control disc, when the shaft itself is bent, added tension to the control cable 44 will force the control mounting disc 42 to move from its neutral position to a tilted position as is shown in FIG. 25 and result in the distal end 16 being moved to an undesired angular position. For example, if one was to take both hands, grasp the shaft at the midpoint and bend it to the position in FIG. 24, tension would be applied to the upper cables, the tip would rise to the position as in FIG. 22 and the disc would tilt inwards at 12 o'clock. Further adjustment would be impaired. However, if the cables are first unlocked from the disc and then the shaft bent at the midpoint, little tension will be applied to the disc or distal tip and so should stay in the "neutral" position. After the cables are locked, full functionality is restored. Using the unlocking and un-locking device herein described, pre-bending of the shaft does not limit further adjustments of the tip.

It should be appreciated that the first configuration of the bendable shaft 18 does not have to be substantially straight as is shown in FIG. 19. The first configuration of the shaft 18 can be, for example, a curved configuration as is shown in FIG. 22. The second configuration could be another bent configuration, for example, which is different from the first configuration. It could also be a substantially straight configuration. Thus, the present invention is designed to remove tension from one or more control cables (by effectively lengthening that cable) as the bendable shaft is bent from one configuration to another.

The present invention utilizes in one embodiment a loop formed on each control wire to allow the relative initial length of the control cable to be changed after the shaft is to be bent to a new configuration. The loop structure provides a simple arrangement which allows the user to quickly change the length of the cables whenever the shaft needs to be re-shaped to a new configuration. This re-shaping can occur in several ways. For example, with the malleably-configured embodiment, the shaft is configured outside the oral cavity. If utilizing a conduit, whether natural or artificial, the device is unlocked, inserted into the conduit, allowing the shaft to return to "neutral," and then locked, allowing full functionality to be restored. Other mechanisms could be utilized to allow the initial length of the cable to be changed whenever the shaft is to be re-bent to a new configuration without departing from the spirit and scope of the present invention.

Again, while the present invention is shown and described as an endoscopic instrument used in a tracheal intubation procedure, it should be appreciated that the present invention can be used in a number of medical procedures and can be adapted in size and shape to fit other body cavities of the patient. For example, the endoscopic version of the device could be used in nasal intubation in which the endotracheal tube is inserted through the nasal cavity, rather than the oral cavity, in order to intubate the patient. Nasal intubation is often used during oral surgeries. In such a case, the endotracheal tube is initially mounted to the shaft of the endoscopic device and then the distal end of the shaft is inserted into the nasal cavity. If the shaft of the device has some rigidity, the shaft could be initially shaped to fit the anatomy of the patient. The endoscopic tube and shaft of the device can then be moved simultaneously into the area adjacent to the opening of the trachea. The steerable distal end of the shaft can be used to steer the endotracheal tube into the trachea. The visualization components of the endoscopic device will assist the practitioner in steering the distal end of the shaft and the endotracheal tube into proper position.

The device described herein can be made from medical grade materials which allow the device to be properly sterilized for each new use. The material could incorporate biocide chemistry which enhances the sterilization process. It should be appreciated that the shaft could have different portions having different rigidities, as is described above. The distal end, for example, could be made from substantially softer materials than the flexible or malleable shafts, which would allow the distal end to react preferentially to tension being applied at the distal end. The distal end and tip would then flex more than the shaft, allowing fine control at that portion. The control cables can be made from plastic or suitable metals or metal alloys. The control case can be made from suitable elastomeric materials which allow for some stretching. The control mounting disc likewise can be made from suitable medical grade materials. The visualization equipment (video screens, optical cables/fibers, batteries) used with the device can be commercially available equipment. The video screen can be removably mounted to the outer casing and the battery pack likewise be removable from the handle portion to allow these components to be removed prior to placing the device in the sterilizing solution. Accordingly, the video screen and battery pack would utilizes quick release electrical connecters which would be incorporated into the outer casing of the device. Such connectors are well known in the art.

While particular forms of the invention have been described and illustrated, it will also be apparent to those skilled in the art that various modifications can be made without departing from the spirit and scope of the invention. Accordingly, it is not intended that the invention be limited except by the appended claims.

What is claimed:

1. A steerable device, comprising:
   a shaft having a lumen extending there through and a steerable, flexible, distal end, and a proximal end;
   a rigid member extending from said proximal end of said shaft;
   at least one control cable having first and second ends with an intermediate portion between said ends, wherein said control cable extends through the lumen of the shaft, with the first and second ends affixed to the flexible, steerable distal end of the shaft; and
   a steering control mechanism coupled to said intermediate portion of the control cable, the steering control mechanism comprising a control disc pivotally mounted on said rigid member enabling tilting of said control disc relative to said rigid member, and having a surface with an axis across which the intermediate portion of said at least one control cable extends and being adapted to move at least one control cable segment, to cause the steerable distal end to move to different angular positions, the steering control mechanism including a locking mechanism comprising a fastener moveable toward said control disc surface along said axis for locking the intermediate portion of said at least one control cable to the control disc surface and away from said control disc surface in the direction of said axis for unlocking said the intermediate portion of said at least one control cable to allow said the intermediate portion of said at least one control cable to be re-positioned relative to steering control mechanism.

2. The device of claim 1, wherein at least a portion of the shaft is made from a malleable material.

3. The device of claim 1, wherein the shaft has a length and a rod made from a malleable material extends within the lumen of the shaft for at least a portion of the length of the shaft.

4. The device of claim 1, wherein said shaft is bendable and wherein at least as portion of the bendable shaft is made from a length of tubing made from a malleable material.

5. The device of claim 1, wherein said shaft has a section of varying rigidity and wherein the distal end of the shaft is made from a material which is more deformable than said section of the shaft which has varying rigidity.

6. The device of claim 1, wherein said shaft is bendable and further including an outer casing in which the steering control mechanism is housed and visualization components incorporated into the shaft and outer casing, the visualization components including a lens located at the distal end of the bendable shaft.

7. The device of claim 1, wherein the steering mechanism is hermetically sealed within an outer casing.

8. The device of claim 1, wherein the shaft is flexible.

9. The device of claim 1, wherein each control cable end has an initial length extending from the steering control mechanism to its distal end when locked by the fastener, the initial length of each end being changeable to a different length by unlocking the end from the locking mechanism, re-positioning the end relative to the locking mechanism, and re-locking the end to the locking mechanism by moving, the fastener toward the control disc surface.

10. A medical device for placement within a body cavity, comprising:
an outer casing having an axis;
a shaft of variable rigidity coupled to the outer casing, the shaft having a lumen extending there through and a flexible, steerable distal end movable to a multiplicity of angular positions;
a rigid member extending within said outer casing, along said axis;
at least one control cable having first and second ends with an intermediate portion between the first and second ends, wherein said at least one control cable extends through the lumen of the shaft with the first and second ends affixed to the flexible, steerable distal end of the shaft; and
a steering mechanism housed within the outer casing and pivotally mounted on said rigid member, said mechanism having a surface with an axis across which the intermediate portion of said at least one control cable extends and comprising an externally threaded screw mounted for movement in the direction of said axis toward said surface to lock said intermediate portion of said control cable to said surface and away from said surface along said axis to release said intermediate portion of said control cable such that said control cable can be moved relative to said surface such that movement of the steering mechanism relative to said rigid member moves the control cable to change the position of the steerable distal end.

11. The medical device of claim 10, wherein the at least one control cable is hermetically sealed within the shaft and outer casing.

12. The medical device of claim 10, further including visualization components which extend through the outer casing and the lumen of the shaft and are coupled to the steerable distal end, the visualization components being hermetically sealed within the shaft and outer casing.

13. A steerable device, comprising:
a shaft having varying rigidity having a lumen extending there through and a flexible, steerable distal end, the shaft being bendable from a first configuration to a second configuration;
said shaft having a proximal end;
a rigid member extending from said proximal end of said shaft;
at least one control cable having first and second end portions with an intermediate portion between said end portions, wherein said first end portion has a first end and said second end portion has a second end, wherein said at least one cable extends through said lumen of the shaft with said first and second ends affixed to the flexible, steerable distal end of the shaft; and
a steering control mechanism having a surface with a central axis pivotally mounted to said rigid member and comprising a fastener moveable toward and away from said surface along said central axis for releasably attaching the intermediate portion of the control cable to said steering control mechanism surface, the steering control mechanism being adapted to move the control cable causing the steerable distal end to move to different angular positions, each control cable end portion having a length measured between the location on the surface of the steering control mechanism to which said intermediate portion of the control cable is attached and the end of said shaft to which the end of said control cable is attached, wherein the relative lengths of the control cable end portions can be changed when the shaft assumes its second configuration by detaching the intermediate portion of the control cable from said steering control mechanism surface.

14. A steerable instrument, comprising:
a control case having an axis;
a shaft with a steerable distal end and a proximal end rigidly attached to the control case;
a rigid member situated within said control case having an end with a pivot point situated along said axis;
at least one control cable having first and second ends with an intermediate portion between said ends, wherein said control cable extends through said lumen of the shaft, with the first and second ends affixed to the flexible, steerable distal end of the shaft; and
a steering control mechanism for moving the steerable distal end of the shaft into a number of different angular positions, wherein the mechanism is manually movable and comprises a control disc having a first surface comprising a recess adapted to receive said pivot point of said rigid member and a second surface, opposite said first surface, said steering control mechanism further comprising at least one control cable and a fastener moveable along said second surface of said control disc to lock the control cable to said second surface of said control disc, said at least one control cable being attached to the steerable distal end of the shaft and to the disc; and wherein the mechanism is configured such that when pressure is applied to the control disc near a periphery of the control disc, the control disc tilts relative to said axis, causing the at least one control cable to be pulled to move the steerable distal end of the shaft into different angular positions.

15. The instrument of claim 14, further comprising a biasing member configured to provide a biasing force on the control disc such that the control disc is moved back to a neutral position when pressure is removed from the control disc.

16. The instrument of claim 14, wherein the control disc includes openings which are adapted to receive projections formed on the control case, such that the connection of the projections into the openings prevents the control disc from rotating.

17. The instrument of claim 14, wherein the shaft is malleable and bendable.

18. The instrument of claim 14, further comprising additional control cables attached to the control disc and the steerable distal end.

19. The instrument according to claim 14, wherein said fastener is configured to allow the at least one control cable to be temporarily freed from the control disc when the shaft is to be bent to a new configuration.

20. The instrument of claim 14, further comprising visualization and illumination components incorporated into the instrument through an internal lumen of the shaft.

21. The instrument of claim 14, further comprising an outer casing and wherein the control case is configured to maintain a hermetic seal to the outer casing.

22. The instrument of claim 17, wherein the malleable shaft comprises a deformable tubing having a length and a lumen formed therein and a malleable rod extending at least partially along the length of the deformable tubing.

23. The instrument of claim 14, wherein the control disc freely articulates on a pivot member.

24. A steerable device, comprising:
a shaft having a proximal end and a steerable, flexible distal end;
a rigid member extending from said proximal end of said shaft and having an end;
at least one control cable comprising first and second distal ends extending through said shaft and an intermediate portion between said distal ends, said distal ends being attached to said shaft at different locations thereon proximate said distal end of said shaft; and
a steering control mechanism mounted on said end of said rigid member for movement relative to said rigid member and having a surface with a central axis, a fastener, said intermediate section of said control cable extending across and being releasably attached to said steering control mechanism surface by movement of said fastener along said central axis toward and away from the steering control mechanism surface, wherein movement of said steering mechanism relative to said rigid member causes said steerable distal end of said shaft to move to different angular positions when said fastener attached the intermediate portion of the control cable to the steering control mechanism surface.

25. The device of claim 24 wherein said fastener comprises an internally threaded member extending from said disc surface and an externally threaded fastener adapted to be received within said internally threaded member.

26. The device of claim 24 further comprising a second control cable comprising a first end and a second l end, a an intermediate section between the first and second ends, wherein the second control cable extends through the lumen of the shaft with the first and second ends affixed to the flexible, steerable end of the shaft, said intermediate section of said second control cable being attached to said steering control mechanism surface such that movement of said steering mechanism relative to said rigid member causes said steerable distal end of said shaft to move to different angular positions.

27. The device of claim 26 wherein said intermediate section of said first control cable and said intermediate section of said second control cable overlap.

28. The device of claim 26 wherein said intermediate section of said first control cable and said intermediate section of said second control cable are attached to said control mechanism surface by said fastener.

29. The device of claim 26 further comprising a fastener and wherein said intermediate section of said first control cable and said intermediate section of said second control cable are attached to said control mechanism surface by the same fastener.

30. The device of claim 26 wherein said intermediate section of said cable and said intermediate section of said second cable intersect over said steering control mechanism surface.

31. A steerable devise, co uprising:
a casing, a rigid member extending within, said casing comprising an end with a pivot point, a shaft extending from said casing and having a steerable, flexible, distal end in a position;
at least one control cable being under tension when said shaft is bent, said cable extending through said shaft and having first and second ends attached to said shaft proximate said distal end of said shaft and an intermediate section extending between said first and second ends of said control cable; and
a steering control mechanism comprising a control disc having a first surface with a recess adapted to receive said pivot point of said rigid member end for movement relative to said rigid member to adjust the position of said distal end of said shaft and having a second surface, said second surface being oppositely directed from said first surface and having an axis, said intermediate section of said control cable being attached by a fastener movable along said axis of said second surface in a position adjustable manner in order to relieve the tension on said cable resulting from the bending of said shaft.

32. A steerable device, comprising:
a casing having a central axis, a shaft having a proximal end and having a steerable, flexible, distal end; a rigid member extending within said casing and having an end;
at least one control cable being under tension when said shaft is bent, said cable extending through said shaft and having first and second ends attached to said, shaft proximate said distal end of said shaft and an intermediate section extending between the first and second cable ends; and
a steering control mechanism situated within said casing, pivotally mounted to said end of said rigid member and attached to said control cable to position the distal end of the shaft, said steering control mechanism having a surface with an axis and being mounted for movement relative to said rigid member to set the position of said distal end of said shaft, a fastener rotationally mounted on said steering control mechanism for linear movement along said surface axis, said intermediate section of said control cable being detachable from and moveable relative to said steering control mechanism surface by the rotation of said fastener in order to relieve the tension on said cable resulting from the bending of said shaft.

33. A steerable device, comprising:

a shaft having a lumen extending there through and a steerable, flexible, distal end, and a proximal end;

a rigid member extending front said proximal end of said shaft;

a firsts control cable having first and second ends with an intermediate portion between said ends, wherein said control cable extends through the lumen of the shaft, with the first and second ends of said first control cable affixed to the flexible, steerable distal end of the shaft;

a second control cable having first and second ends with an intermediate portion between said ends, wherein said control cable extends through the lumen of the shaft, with the first and second ends of said second control cable affixed to the flexible, steerable distal end of the shaft; and a steering control mechanism coupled to the intermediate portions of the first and second control cables, the steering control mechanism comprising a control disc pivotally mounted on said rigid member enabling tilting of the control disc relative to said rigid member, the control disc having a surface with an axis across which the intermediate portions of the first and second control cables overlap each other, the steering mechanism adapted to selectively move the first and second control cables to cause the flexible, steerable distal end to move to different angular positions, the steering control mechanism including a locking mechanism for locking the intermediate portions of the first and second cables to the control disc surface and for unlocking the intermediate portions of the first and second control cables to allow the intermediate portions of the first and second control cables to be repositioned relative to the control disc, wherein the locking mechanism is a fastener moveable along said axis of said control disc surface that releasably engages the intermediate portions of the first and second control cables.

34. The device of claim 33 wherein said fastener comprises an externally threaded section.

35. The device of claim 34 further comprising a member attached to said disc surface defining an internally threaded opening adapted to receive said section of said fastener.

36. The device of claim 35 wherein said member defines a channel with the disc surface and wherein said intermediate portions of said first and second control cables pass through said channel.

37. The device of claim 36 wherein said channel is located between said member opening and said disc surface.

38. The device of claim 33 wherein said disc surface has an axis and wherein said fastener moves along said disc axis.

* * * * *